United States Patent [19]

Ledley et al.

[11] Patent Number: 4,817,119

[45] Date of Patent: Mar. 28, 1989

[54] METHOD AND APPARATUS FOR COMPUTERIZED TOMOGRAPHIC SCANNING WITH PLURAL INTERSECTING SETS OF PARALLEL RADIATION BEAMS

[75] Inventors: Robert S. Ledley, Silver Spring, Md.; James B. Wilson, Arlington, Va.

[73] Assignee: National Biomedical Research Foundation, Washington, D.C.

[21] Appl. No.: 827,772

[22] Filed: Aug. 25, 1977

[51] Int. Cl.$^4$ .............................................. H05G 1/00
[52] U.S. Cl. ........................................ 378/9; 378/4; 378/19
[58] Field of Search ............... 250/445 T, 439 R, 444, 250/445 R, 446, 447, 448, 449, 490, 523, 358 R, 359, 360, 363 R; 378/4, 9, 11, 19

[56] References Cited

U.S. PATENT DOCUMENTS

| | | | |
|---|---|---|---|
| 4,010,370 | 3/1977 | LeMay | 250/445 T |
| 4,031,395 | 6/1977 | LeMay | 250/445 T |
| 4,057,725 | 11/1977 | Wagner | 250/445 T |
| 4,093,863 | 6/1978 | Zacher, Jr. | 250/445 T |

*Primary Examiner*—Craig E. Church
*Attorney, Agent, or Firm*—Joseph G. Seeber

[57] ABSTRACT

An array of radiation detectors is rotated about one or more sources of fan-shaped substantially planar radiation beams which are, in turn, rotated in the opposite direction about a three-dimensional body such that substantially parallel paths are defined between given individual detectors of the array and the radiation sources during the course of their oppositely directed movements. Radiation absorption measurements are taken along thusly defined plural intersecting sets of substantially parallel paths within a desired cross-section of the three-dimensional body to provide data for use in computing and displaying a constructed visual image of structures having different radiation absorption coefficients within the cross-section.

84 Claims, 14 Drawing Sheets

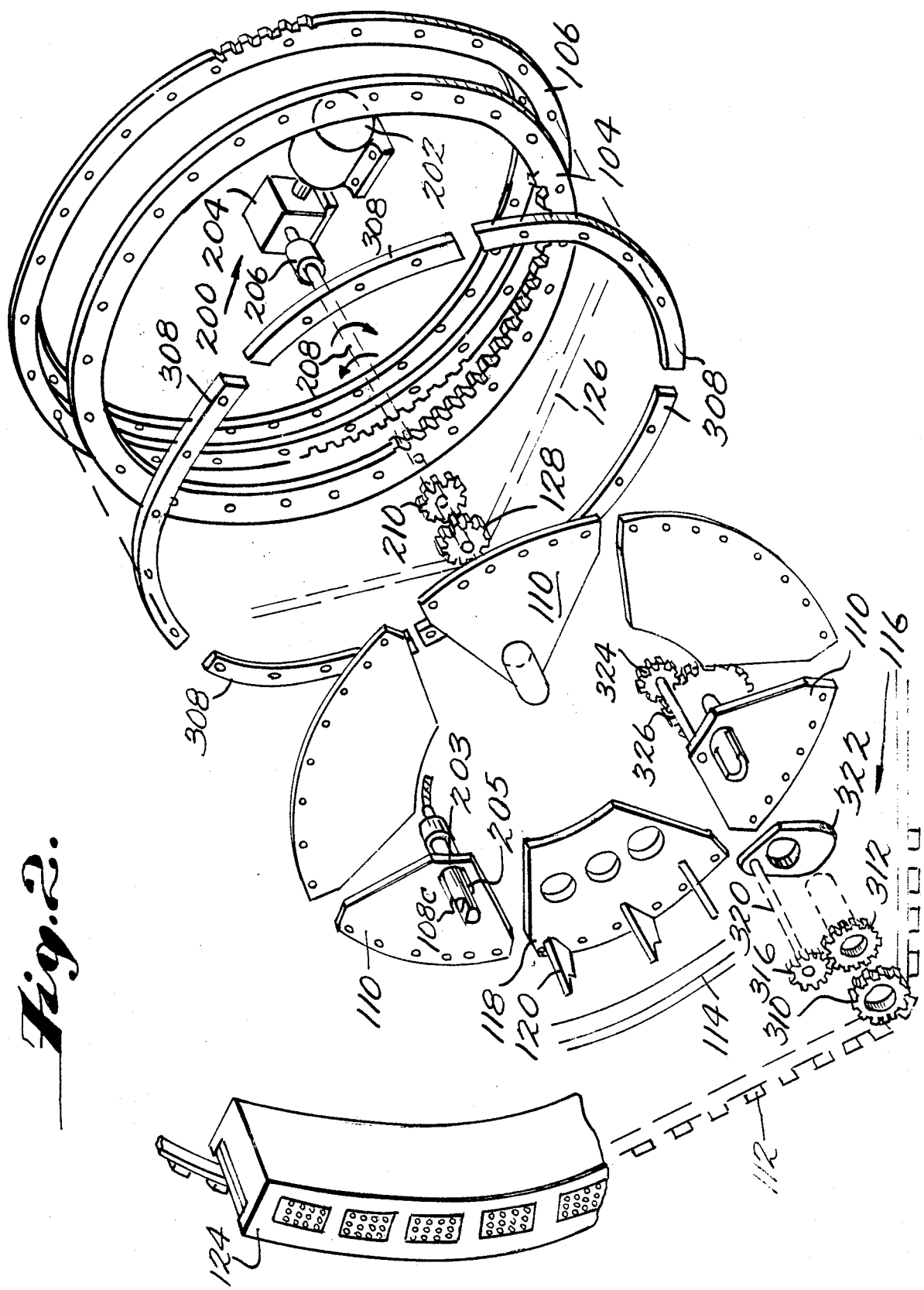

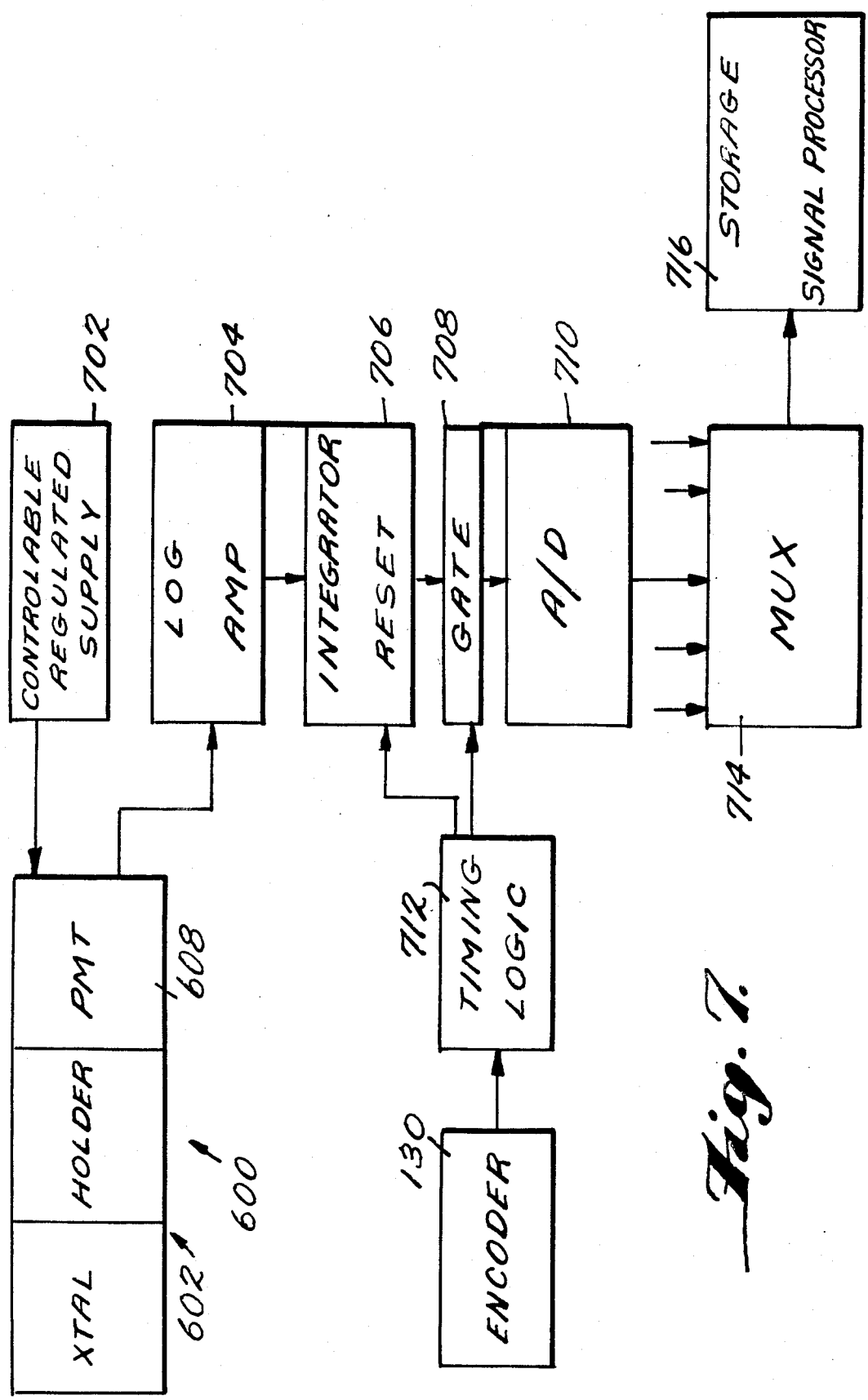

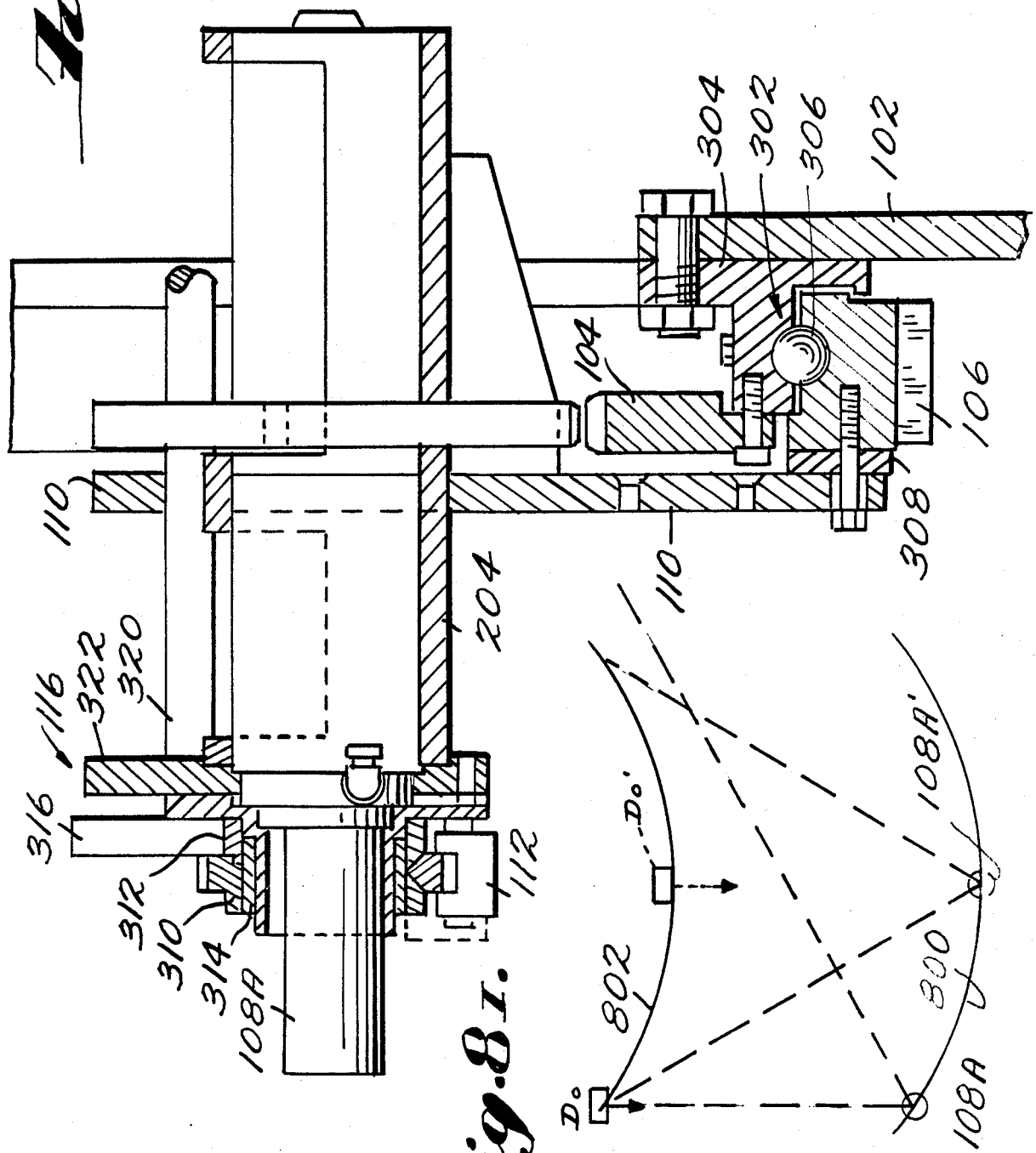

METHOD AND APPARATUS FOR COMPUTERIZED TOMOGRAPHIC SCANNING WITH PLURAL INTERSECTING SETS OF PARALLEL RADIATION BEAMS

This invention is generally concerned with method and apparatus for computerized tomographic scanning with beams of X-ray or gamma ray radiation.

Other computerized tomographic scanning techniques and apparatus are disclosed in commonly assigned U.S. Pat. Nos. 3,922,552 issued Nov. 25, 1975 and 4,005,311 issued Jan. 25, 1977 to Robert S. Ledley. Commonly assigned pending U.S. Pat. application Ser. No. 803,783 filed Jun. 6, 1977 also discloses other computerized tomographic scanning techniques and apparatus.

Computerized tomographic scanning generally involves measuring radiation beam transmissions within a cross-section of a three-dimensional body along plural intersecting paths to provide data which is utilized by a programmed computing apparatus in constructing a cross-sectional depiction of structures within the three-dimensional body having differing radiation absorption properties. Although presently used primarily to depict living tissues (e.g., human bodies) the same techniques can also be used for inanimate objects as will be appreciated.

A desired cross-section of a patients's body is positioned between one or more radiation sources (e.g., X-rays or gamma rays) and a radiation detector system. The radiation beams emanating from the source are attenuated during passage through the body section as some of the beam is absorbed while the remainder is passed or transmitted through the body to be detected by, for example, a scintillation crystal which produces light photons in response to incident radiation. The light photons are in turn converted to electrical signals by, for example, a photomultiplier tube as will be appreciated by those in the art.

The magnitude of radiation transmission by the body section along any given beam path is a function of the sum of the radiation absorption coefficients of the various body tissues through which such beam passes. The absorption coefficients of the respective tissues are, in turn, related to their electron densities where the radiation involved is in the X-ray spectrum.

The transmission or absorption of radiation beams impinging upon the body section from a large number of angles is measured and recorded so as to provide data used in calculating an array of point-by-point relative absorption coefficients for the body section under investigation. These computed coefficients or other equivalent data are then visually displayed in a two-dimensional visual array having respectively corresponding visual properties so as to provide a computed pictorial depiction of the cross-section in question.

For a more detailed description of the various types of prior tomographic scanners, reference is made to: "Computerized Transaxial X-ray Tomography of the Human Body," Science, Oct. 18, 1974, Vol. 186, pp. 207-212, by Dr. R. S. Ledley et al; "Introduction to Computerized Tomography," Computers in Biology and Medicine, Pergeamon Press, 1976, Vol. 6, pp. 239-246 by Dr. Ledley; and "Recent Advances in Computerized Tomography," Proceedings of the IEEE International Conference on Cybernetics and Society, Washington, D.C., Nov. 26, 1976 by Doctors Ledley and Huang.

Additionally, reference may be had to the following prior issued United States patents for other techniques and apparatus proposed and/or used in the past by others in the field of computerized tomographic scanning: U.S. Pat. Nos. 3,778,614- Hounsfield (1973); 3,881,110-Hounsfield et al (1975); 3,924,129 - LeMay (1975); 3,924,131-Hounsfield (1975); 3,932,757- Hounsfield (1976); 3,934,142-Hounsfield (1976); 3,936,636- Percival (1976); 3,937,963-Hounsfield (1976); 3,940,625- Hounsfield (1976); 3,940,626-Hounsfield (1976); 3,946,234- Hounsfield (1976); 3,952,201-Hounsfield (1976); 3,965,357- Hounsfield (1976); 3,973,128-LeMay (1976); 3,999,073- Hounsfield et al (1976); 4,002,911 Hounsfield (1977); 4,010,370- LeMay (1977); 4,010,371 LeMay (1977); and 4,031,395 - LeMay (1977).

Some of these earlier tomographic scanners use a highly collimated single X-ray beam and aligned detector on the opposite side of the body. This single beam is translated in synchronism with the movable aligned detector so as to scan the body section along plural parallel beam paths. After one such set of parallel path measurements is effected, the entire device is rotated with respect to the body section. Thereafter, the radiation beam and aligned detector are translated to provide yet another set of parallel path measurements which intersect with earlier sets of parallel path measurements. The resulting measurements from these plural intersecting sets of parallel paths are utilized in computing an array of point-by-point relative absorption coefficients which are displayed visually in a cross-sectional depiction of the body section under examination. See, for example, the earlier referenced U.S. Pat. Nos. 3,778,614; 3,924,129; 3,924,131; 3,932,757; 3,936,636; 3,946,234; 3,965,357; and 4,002,911. Algorithms for processing the parallel beam measurements are known, for example, from "Three-dimensional Reconstruction from Radiographs and Electron Micrographs; Application of Convolutions Instead of Fourier Transforms" by G. N. Ramachandran and A. V. Lakshminarayanan The Proceedings of the National Academy of Sciences, U.S.A., Vol. 68, No. 9, p. 2236, September, 1971 and from "The Fourier Reconstruction of a Head Section" by L. A. Shepp and B. F. Logan, IEEE Transactions on Nuclear Science, Vol. NS21, June 1974.

However, such earlier parallel beam scanning techniques require a considerable time interval to acquire the necessary data for computing the cross-sectional depiction. Accordingly, to reduce the data acquisition time interval, substantially planar fan-shaped beams of radiation were later used in conjunction with arrays of individual radiation detectors so as to simultaneously acquire radiation absorption data for a number of divergent beam paths thus reducing the overall data acquisition time interval. In general, the radiation detector arrays utilized in such fan beam scanning techniques have been either fixed with respect to the moving radiation source or rotated in unison and in the same direction with the radiation source. See, for example, the earlier referenced U.S. Pat. Nos. 3,881,110; 3,934,142; 3,937,963; 3,940,625; 3,940,626; 3,952,201; 3,973,128; 3,999,073; 4,010,370; 4,010,371; and 4,031,395.

Although the use of fan-shaped beams and plural detector arrays has significantly reduced the necessary data acquisition time, the necessary data computation time for such fan beam techniques is significantly increased due to the more complex algorithm required for processing the divergent (non-parallel) fan-shaped sets of intersecting radiation absorption beam measurements which usually result from use of a fan beam. Furthermore, in the fan beam systems which utilize fixed detector arrays, it is often impossible to use collimators on the detectors because of the different angles from which radiation is incident on the detector. In such circumstances, a less sensitive scintillation crystal is often used, thus necessitating an increase in the radiation exposure suffered by the patient under examination. There are other costs and/or technical disadvantages normally associated with the prior fan-shaped beam techniques as will be appreciated by those in the art.

Recently issued U.S. Pat. No. 4,010,370-LeMay (1977) represents one attempt to provide absorption data for plural intersecting sets of parallel beams (thus permitting use of the favored "parallel beam" algorithm) in spite of the fact that a fan-shaped planar beam radiation source is employed. LeMay shows an X-ray source fixed with respect to a detector array. Both the source and the detector array are rotated about a body under examination. However, in LeMay's preferred embodiment, a special scanning X-ray tube is used so as to cause the fan beam to undergo periodic scanning motion in a direction opposite the ongoing rotation of the source. In the embodiment of LeMay's FIG. 7, a counter rotating ring of collimators causes similar periodic scanning of incremental angular sections followed by rapid flyback to initiate another increment of scanning. LeMay teaches a rather elaborate interlaced mapping of the successive detector outputs produced by his incremental scanning process onto predetermined elements of plural data storage arrays so as to eventually accumulate data representing radiation absorption measurements for plural intersecting sets of parallel paths.

The recently issued LeMay U.S. Pat. No. 4,031,395 is in many respects similar in operation to the just discussed LeMay '370 patent in that an array of detectors is fixed with respect to an X-ray source which is successively scanned thereover at a plurality of locations about the body under examination. Other alternative embodiments are described (e.g., column 5, lines 8 et seq., and column 6, lines 18 et seq.) wherein the X-ray source is mechanically or electrically scanned completely about the subject in cooperation with a fixed array of detectors.

Now, however, it has been discovered that the method and apparatus of this invention effectively combines many of the advantages of the earlier "parallel beam" and "fan beam" techniques while avoiding most if not all of the disadvantages earlier associated with these techniques. In so doing, this invention is believed to be an improvement in many respects over the LeMay periodic scanning technique just described.

According to this invention, a substantially planar beam of radiation (e.g., fan-shaped) is continuously rotated in a first direction with respect to a three-dimensional body under examination. At the same time, after passage through the body, the planar beam is scanned by plural detectors rotating continuously in a second direction opposite the first direction centered about the radiation source. This complex superposed motion of the detectors defines plural intersecting sets of parallel paths terminating on corresponding individual detectors in the array along which radiation absorption measurements are taken. As will be explained, this complex motion results in a given detector traversing an arc parallel to the arc being transversed by the radiation source at a constant distance therefrom. At the same time, the detector is constantly directed or aimed toward the radiation source thus producing constant response characteristics from the scintillation crystal. This constant relative orientation also permits the use of detector collimators and highly sensitive CaFl scintillation crystals.

In the presently preferred exemplary embodiment of this invention three radiation sources are spaced at 120 degree intervals about the patient. Each source directs a fan-shaped substantially planar beam of radiation through a cross-section of the patient and between the remaining two sources. This whole array of sources is mounted for rotation, in unison, about an axis substantially perpendicular to the co-planar fan beams such that the desired patient cross-section is completely scanned with radiation emanating from all angles after a rotation of the source array by only 120 mechanical degrees.

At the same time, in the presently preferred exemplary embodiment of this invention, an endless array of radiation detectors is disposed on three intersecting arcs, each arc being opposite and equidistant from a respectively associated radiation source. This endless detector array is, during operation, continuously moved along the intersecting arcs in the opposite direction from the rotation of the sources thus, in effect, rotating about the sources. By causing such continuous and equal but opposite rotational movement of the fan beam sources and the detector array (the array motion along a given arc actually being the complex resultant of two superposed rotational motions) plural intersecting sets of substantially parallel paths are defined between the sources and various individual detectors. In this exemplary embodiment two oppositely directed measurements are provided along each set of parallel paths although only a very few individual detectors are needed to define a given set of parallel paths.

Accordingly, in this presently preferred embodiment, three equally spaced, point X-ray sources of planar fan-shaped beams rotate in one direction while multiple detectors move on an eccentric track composed of three arcs in the opposite rotational direction. A given detector is always pointing directly toward one of the X-ray sources and at a constant distance therefrom and, as a result, a collimator is preferably mounted at each detector.

The detectors move on the arcs so as to complete equal but opposite angular movements with respect to the sources. Consequently a given detector scans through different portions of a fan-shaped beam to define a set of parallel paths, beams or rays in each successive arc over which it passes. As a given detector passes a cusp along the detector track, it begins a differently oriented set of parallel beam measurements. To reduce the necessary measurement time, one set of parallel beam measurements may be completed by combining data from two different detectors. Angular movement of the sources and detectors about the axis of the scanner are preferably both continuous and oppositely directed through 120 degrees. Individual beam width is defined by a timing circuit controlling the integration and sampling times associated with each data measurement to be taken from a given detector.

Since this invention provides radiation absorption measurements along plural intersecting sets of parallel radiation paths, familiar "parallel beam" algorithms may be used in computing and displaying the cross-sectional depiction of the body under examination. As earlier mentioned, "parallel beam" algorithms require a significantly shorter computation time interval. In addition, "parallel beam" algorithms are well known and have been in use longer than other algorithms. The result is a higher quality and more reliable visual depiction. For example, one "parallel beam" algorithm is already available and used in the model 200 tomographic scanner now being marketed by Pfizer Medical Systems of Columbia, Maryland.

The preferred exemplary embodiment of the present invention also permits the use of a collimator on each radiation detector since they are always in alignment with the X-ray source then illuminating the detector. The use of a collimator at each detector permits one to effectively define an X-ray beam having smaller cross-section thus increasing the resolution capability of the machine. While collimators have been used, of course, in some prior art approaches on detectors, most prior art approaches using fan beam techniques have not been able to utilize collimators because of the varying angle between the X-ray source and the detector during normal operation.

Furthermore, in the presently preferred exemplary embodiment of this invention, a highly sensitive calcium fluoride scintillation crystal can be used in combination with the detector collimator. Accordingly, the X-ray or other radiation dosage encountered by the patient with the use of this invention may be approximately one order of magnitude less than that encountered with commercial machines embodying the fan beam technique and utilizing the much less sensitive BGO scintillation crystal.

Because of the unique structure involved in the presently preferred exemplary embodiment of this invention, only approximately 200 detecting stations and associated components, hardware and circuitry are required as compared to approximately 600-700 similar detecting stations normally used in most scanners using the fan beam technique. Since each detecting station and its associated components, hardware and circuitry are quite expensive, this significant saving in the number of detectors while yet providing a very rapid scanning motion, high resolution, high reliability and high quality data manipulation, etc. is a significant advantage.

Additionally, due to the unique geometry of the presently preferred exemplary embodiment of this invention, one effective 360° scan of the cross-section under investigation is achieved while rotating the apparatus through only 120 mechanical degrees. At the same time, each parallel path is actually traced out twice and measured two times (once from each end) rather than only once. Accordingly, after such dual measurements are averaged, the raw data actually supplied to the computing apparatus will have better accuracy and reliability and the resulting visual depiction of the cross-section will be correspondingly improved.

Thus, using the presently preferred exemplary embodiment of this invention, a less expensive yet very fast and reliable apparatus and method are provided. The preferred accurate parallel beam reconstruction algorithm may be used by having detectors rotate counter to the rotation of the radiation sources. The X-ray exposure to a patient is decreased by decreasing the necessary scanning time as well as by decreasing the necessary intensity of the X-ray beam through the use of more sensitive radiation detectors. Furthermore, collimators may be used at each detector and fine detail or close resolution may be achieved in the final visual depiction by defining closely spaced plural intersecting sets of parallel radiation beams.

These, as well as other advantages and benefits of this invention will be better understood by reference to the following detailed description of the presently preferred exemplary embodiment of the invention taken in conjunction with the accompanying drawings wherein:

FIG. 2 is an exploded perspective view of various of the elements of the scanner of FIG. 1;

FIG. 3 is a sectional view of the scanner of FIG. 1 taken at 3—3 of FIG. 1;

FIG. 7 is a block diagram of suitable signal processing circuitry for use with a scanner in accordance with the present invention;

FIG. 8I schematically illustrates the resultant complex motion of the individual radiation detectors with respect to the radiation sources in the scanner of FIG. 1.

DETAILED DESCRIPTION OF A PREFERRED EXEMPLARY EMBODIMENT

Figure 1:
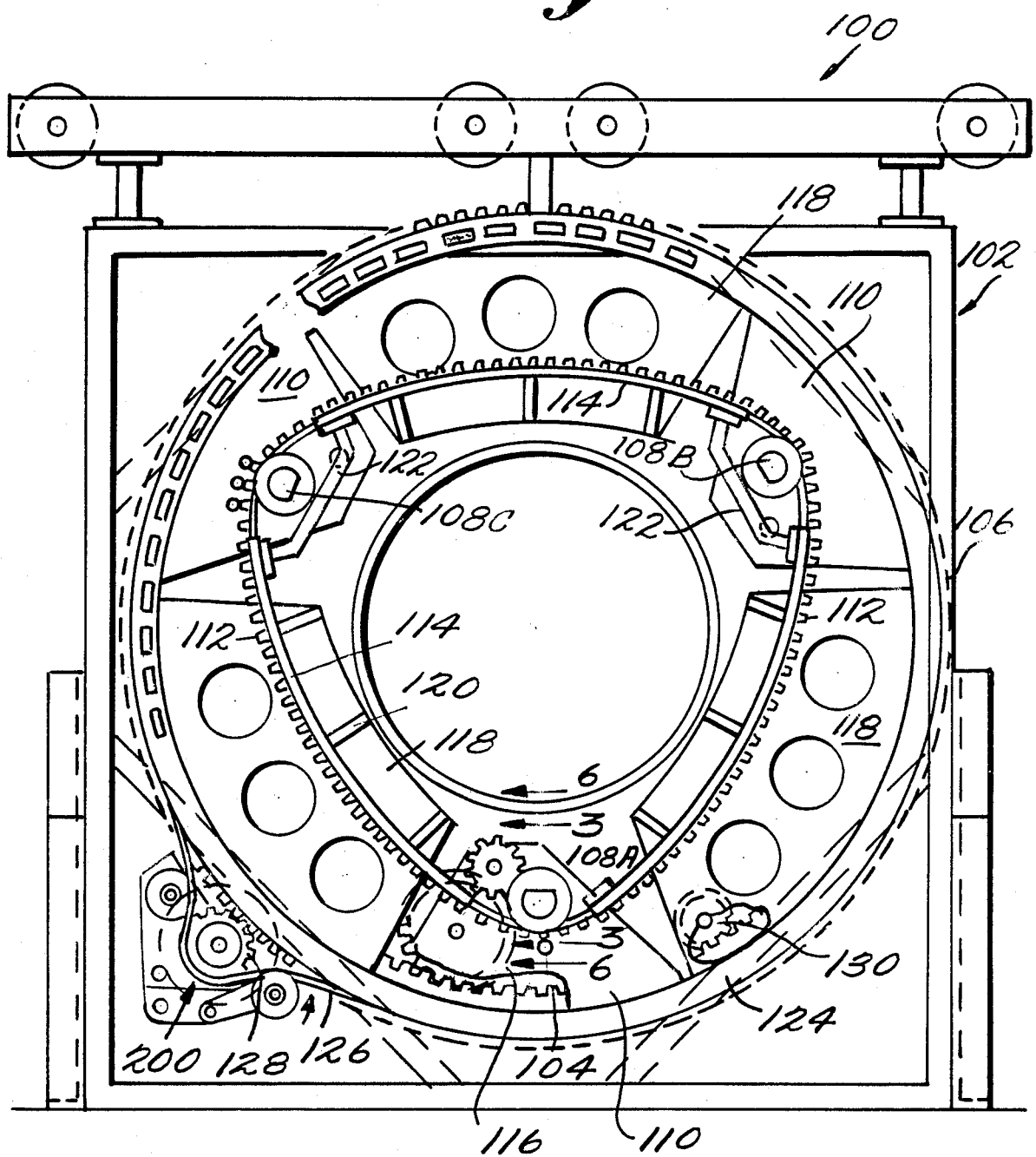
FIG. 1 is a front elevational view of a tomographic scanner in accordance with the present invention.

Referring now to the drawings, wherein like numerals denote like elements, a preferred exemplary embodiment of a tomographic scanner 100 in accordance with the present invention is shown in front elevation in FIG. 1. A frame structure 102, having a generally circular aperture, supports a fixed planetary ring gear 104 secured about the internal perimeter of the aperture. A driven rotating ring gear 106 having teeth about its exterior perimeter is rotatably secured to frame 102 for rotation about the central axis of the aperture.

Referring briefly to FIG. 3, rotating gear 106 is coupled to frame 102 by a bearing assembly, generally indicated as 302, suitably a "Rotek" type bearing comprising an inner race 304, outer race 308 and plurality of bearing balls 306. Inner race 304 is affixed (i.e., by bolting) to frame 102. Gear 106 is supported about inner race 304 by bearing balls 306. Fixed gear 104 is secured (i.e., by bolting) to inner race 304. Thus, gears 104 and 106 are respectively fixedly and rotatably secured to frame 102.

With brief reference now to FIG. 2, rotating gear 106 is driven at a constant speed by a drive assembly, generally indicated as 200. Drive assembly 200 comprises a conventional motor 202 such as, for example, a 3000 rpm DC motor, coupled to a conventional speed reducer 204 such as a "Winsmith" speed reducer model no. SOB, having a 12:1 ratio. Reducer 204 is releasably coupled, by a conventional coupler 206, to a drive shaft 208 passing through frame 102 and rotating a pinion gear 210. Pinion gear 210 engages and meshes with rotating ring gear 106. The ratio of the ring gear 106 to pinion 210 is such that gear 106 revolves once for every 11.071 revolutions of pinion gear 210.

Referring again to FIG. 1, three conventional X-ray (or other suitable radiation) sources 108A, 108B and 108C, collectively referred to as sources 108, are secured to rotating gear 106, relatively disposed at 120° about a circle within the frame aperture. X-ray sources 108 are secured to rotating gear 106 by respective mounting plates 110. As is best seen from FIG. 2, each X-ray source 108 is received in a corresponding aperture 203 in respective mounting plates 110 having a transverse support structure 205 extending on either side thereof. X-ray sources 108 are fixedly secured to respective support structures 205 and are directed to provide, in cooperation with a suitable shield (not shown), a substantially planar fan beam of predetermined fan-angle, preferably 60°. Mounting plates 110 are secured, as shown in FIG. 3, to rotating gear 106 (i.e., by bolting) and spaced therefrom by spacing blocks 308.

Referring again to FIG. 1, a detector conveyor 112, comprising a continuous chain of cars to which the detectors are mounted, is guided by tracks 114 along eccentric arcs between the respective X-ray sources 108 and centered on the respectively associated diametrically opposed X-ray source. The coupling of the detectors to the cars will be explained in more detail in conjunction with FIG. 6.

Conveyor 112 and tracks 114 are, in the presently preferred embodiment, affixed to gear 106 and rotate in unison with X-ray sources 108. Detector conveyor 112 is supported by track 114 and portions of respective gearing assemblies 116, rotatably mounted about the respective X-ray sources 108, as will be described. Track 114 may be continuous or may comprise three segments as shown, each segment defining a respective arc of predetermined radius between respective X-ray sources 108 and subtending an angle substantially equal to the fan-angle (60°) of the beams from sources 108. Each segment of track 114 is similarly secured to rotating gear 106 by respective mounting plates 118, mounted on gussets 120. Mounting brackets 122 are also provided to secure adjacent track sections to each other in the vicinity of respective sources 108.

Figure 4:
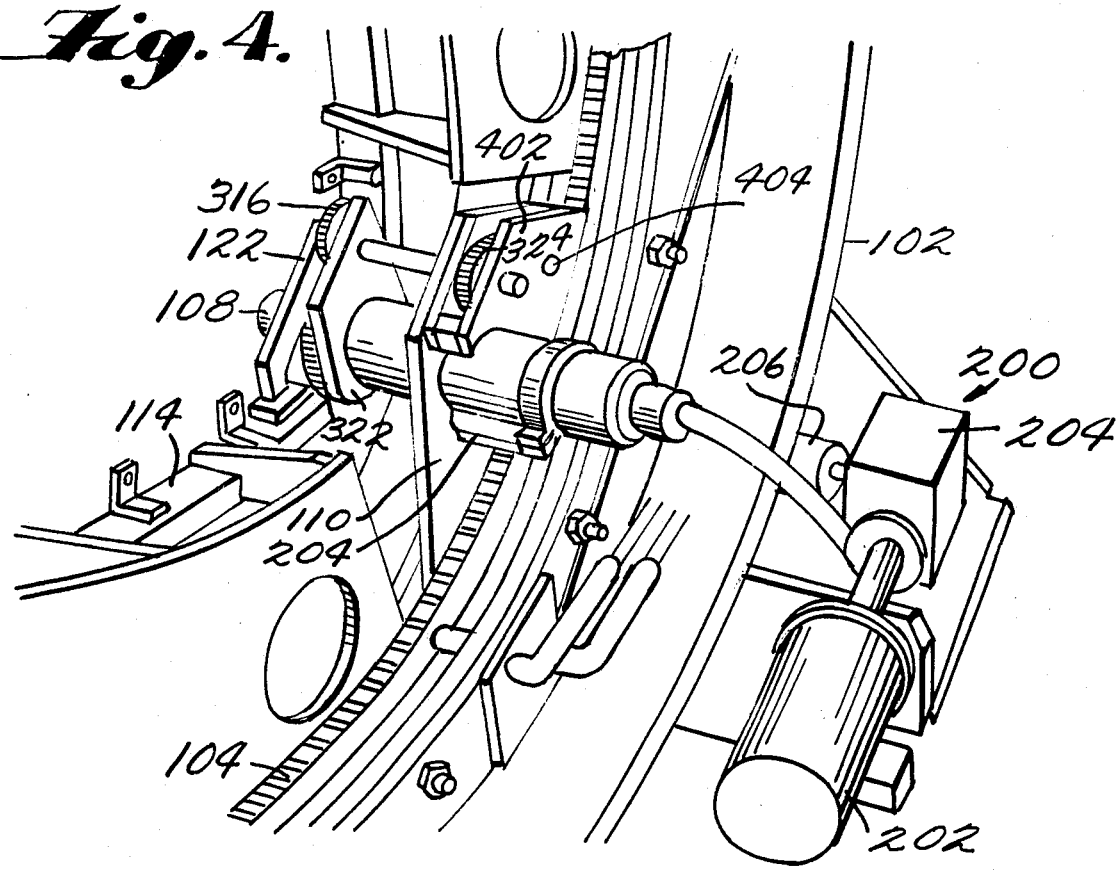
FIG. 4 is a rear fragmentary perspective view of the detector conveyor gear assembly.
Figure 5:
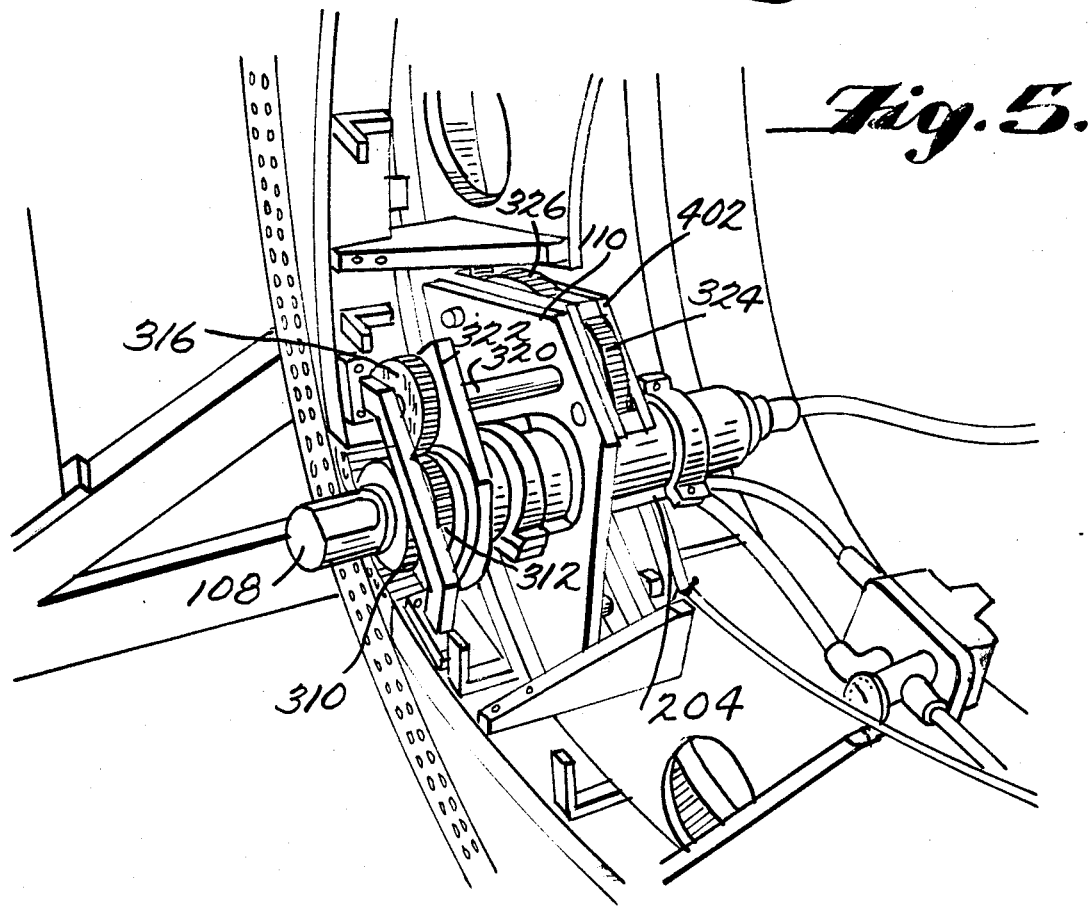
FIG. 5 is a front fragmentary perspective view of the detector conveyor gear assembly.

In accordance with one aspect of the present invention, conveyor 112 is adapted to cooperate with gearing assembly 116 to effect controlled rotation of the individual detectors in a direction opposite to the direction of rotation of X-ray sources 108. With reference now to FIGS. 2, 3, 4 and 5 and specific reference to FIG. 3, the individual cars of conveyor 112 engage a conveyor sprocket wheel 310 directly coupled to a driven conveyor gear 312, both rotatably mounted about an associated X-ray source 108A on a bearing assembly 314. Driven gear 312 engages a gear 316, which is coupled to one end of a shaft 320. Shaft 320 passes through a supportive housing 322 and mounting plate 110 (secured to each by appropriate bearing assemblies) and, as best shown in FIGS. 4 and 5, is coupled on the other side of mounting plate 110 to a gear 324 which, in turn, engages the drive gear 326, drive gear 326 engaging fixed gear 104. One of gears 316 and 324 is preferably a phasing gear to accommodate any phase differences in this sequence of gears. Shaft 320 terminates in a bearing assembly mounted in a further rear support plate 402, best seen in FIG. 4. Drive gear 326 is mounted on a shaft 404 which is rotatably mounted between support plate 110 and rear support plate 402.

The gearing assembly 116 just described effects a movement of the individual conveyor cars 112 in synchronization with, but in opposite rotational direction from, the rotation of ring gear 106. As pinion gear 210 is rotated by drive assembly 200, gear 106 and, accordingly, X-ray sources 108 and (in the presently preferred embodiment) conveyors 112, tracks 114 and gearing assembly 116 are rotated with respect to fixed gear 104. As gearing assembly 116 is rotated along gear 104 in, for example, a clockwise (counterclockwise) direction, drive gear 326, which is rotatably mounted to gear 106, engages with gear 104 to impart a counterclockwise (clockwise) rotation thereto. The engagement between drive gear 326 and gear 324 effects a clockwise (counterclockwise) rotation of gear 324 and, through shaft 320, of gear 316 as well. The engagement of driven gear 312 and gear 316 thus effects a counterclockwise (clockwise) rotation of gear 312. Since sprocket wheel 310 engaging conveyor cars 112 is directly coupled to gear 312, translation of the conveyor in a counterclockwise (clockwise) direction along the arcs defined by tracks 114 is effected.

The respective gearing ratios are chosen such that the movement of each individual detector effectively counteracts the relative rotational movement between the illuminating X-ray source and individual detector thus maintaining a direct path from the X-ray source to the detector at a constant angle with respect to the body section being scanned. For example, in the presently preferred embodiment, drive gear 326 rotates through 8.5719 revolutions while traversing fixed ring gear 104, while each revolution of gear 326 effects 10.470 revolutions of change gear 324. Gears 316 and 312 and sprocket 310 each rotate through one revolution in accordance with one revolution of gear 324.

Referring once more to FIG. 1, a suitable rotary encoder 130, such as a Data Technology Inc., Optecon encoder Model No. 0525-1250-50/5, is also affixed to rotating gear 106 and adapted to cooperate with fixed gear 104. Encoder 130 is suitably secured to detector track mount 118 and includes a geared shaft (not shown) engaging fixed gear 104, such that encoder 130 generates a pulse indicative of every predetermined incremental angle, suitably 1/6°, rotated through by rotating gear 106.

Figure 6:
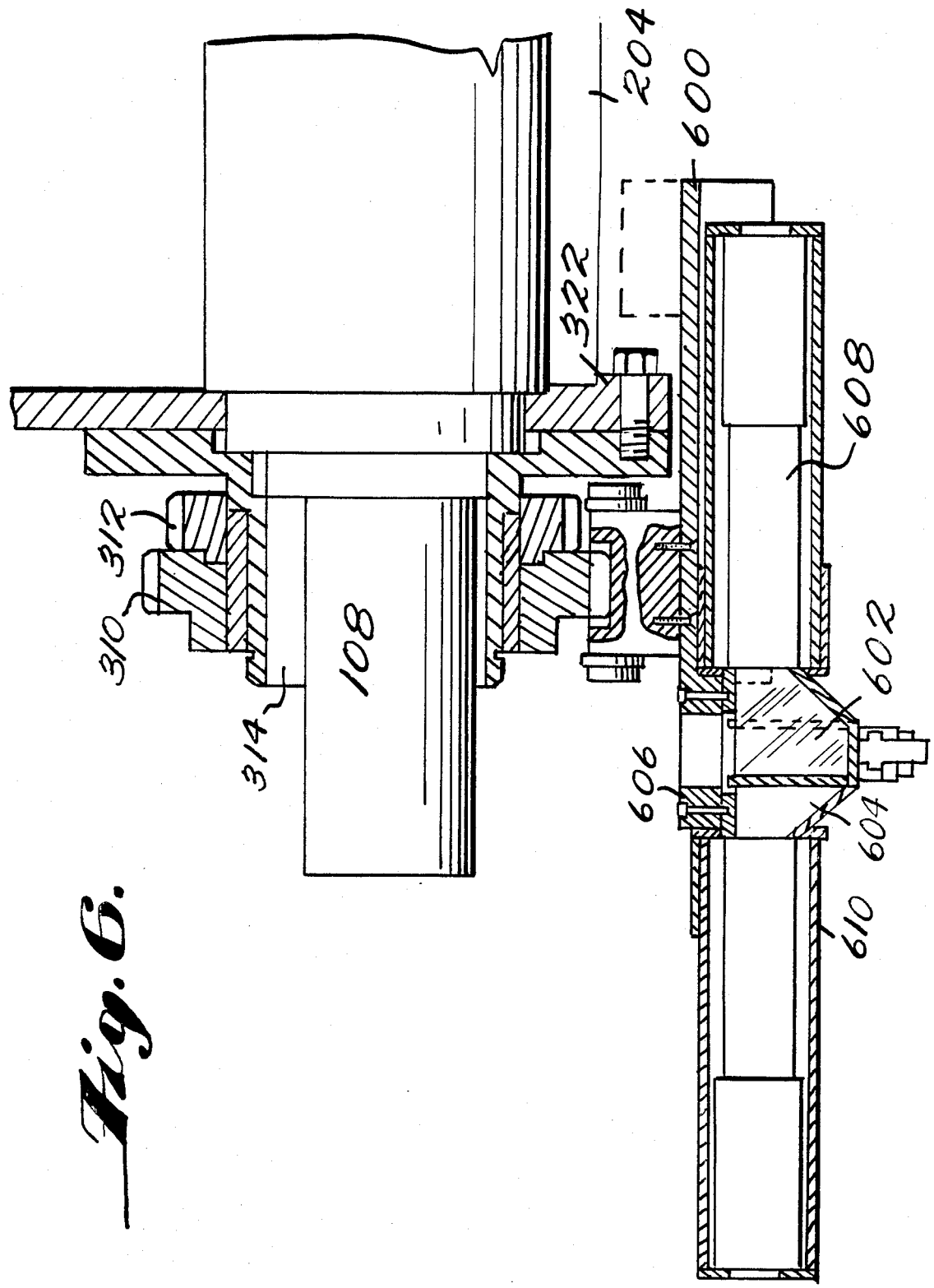
FIG. 6 is a sectional view taken at 6—6 of FIG. 1.

In the presently preferred embodiment, conveyor 112 includes 96 cars, each of which bears two scintillation-crystal photomultiplier-tube detector units. Referring now to FIG. 6, each car of conveyor 112 has affixed thereto (i.e., by bolting) a detector holder assembly 600. Two scintillation crystals 602 and 604 are disposed in light-conducting plastic holders and fixed sideways adjacent and reverse ended to holder 600 in the plane of the X-ray beam. A collimator 606 comprising a block of X-ray impervious material, such as lead, has vertical slits therethrough in alignment with respective detector crystals 602 and 604. Photomultiplier tubes (PMTs) 608 and 610 are fixed to holder 600 with the input faces thereof being set adjacent and optically coupled to the plastic holders of crystals 602 and 604, respectively. An opaque cover is provided over and around each of the plastic holders, such that substantially all light produced by the scintillation crystals is conducted to the PMT associated therewith.

It should be appreciated that each of the 192 PMTs has cables associated therewith to supply power to the PMT and to conduct the output signals of the PMT to the signal processor, as will be described. To prevent snagging and entanglement of the large number of cables, a cable carriage 124 (FIG. 1) is rotatably mounted on rotating gear 106 and driven in synchronization with conveyor 112 by a belt 126 cooperating with a sprocket 128, coupled to drive shaft 208. To maintain synchronization between cable carriage 124 and conveyor 112 in an apparatus having the exemplary gearing ratios and drive mechanism described above, sprocket 128 suitably revolves 12.132714 times to produce one revolution of cable carriage 124.

Referring now to FIG. 7 (PMT 608, for example, there are 192 PMTs) is supplied with operating power by a controlled regulated supply 702. Supply 702 suitably includes a voltage divider (not shown) to control the gain of the respective PMTs. Each PMT output signal is applied to an associated suitable logarithmic amplifier 704 and therefrom to an associated suitable integrator 706. Alternating channels of a two channel dual-slope integrator may be used to permit longer sampling intervals with higher sampling rates. For example, even though a sample integration period of 4 milliseconds is used for each sample, a new sample can still be taken every 5 milliseconds by using alternating channels for successive samples. Each integrator output signal controllably is applied, through a gate 708, to an associated analog to digital (A/D) converter 710. Gate 708 in effect provides a sample of the integrator output signal to A/D converter 710, in accordance with timing signals derived by suitable timing logic 712 in dependence on timing pulses from encoder 130.

A/D converter 710 may be a counter incremented at a constant rate over a period proportional to the integrator output signal, up to a predetermined maximum period, corresponding to, for example, the magnitude of an X-ray beam passing from source to detector without any intervening absorption. Each A/D converter 710 is coupled to a suitable multiplexer 714, for application of the digital data to conventional storage and data processing apparatus, generally indicated as 716. Data processing apparatus 716 suitably comprises a PDP-11 computer cooperating with auxiliary memory units (magnetic disc or tape units or both) and available high-speed convolver and back projector units, such as presently used in the aforementioned Model 200 tomographic scanner marketed by Pfizer Medical Systems of Columbia, Maryland.

Briefly, in operation, the body section to be scanned is disposed in the frame aperture, centrally of X-ray sources 108. Rotating gear 106 is rotated at a constant speed in a predetermined direction by drive assembly 200. As gear 106 rotates, the interaction with fixed gear 104 causes gearing assembly 116 to rotate detector conveyor 112 about the respective sources 108 in a direction opposite to that of the rotation of gear 106 to effectively cancel any change in relative angular orientation of a given respective detector with respect to its respectively associated source.

When the rotating gear 106 reaches a predetermined position, X-ray tubes 108 are activated, each providing, in cooperation with a shield (not shown, a planar fan beam of nominal 60° fan-angle, directed to irradiate the entire body section and the arc of detectors passing between the other two X-ray sources. As mentioned above, the detectors include a scintillation crystal (i.e., 602, 604) which generates light of an intensity representative of the radiation transmission (or absorption encountered) along a given path through the body section. The associated photomultiplier tube (i.e., 608, 610) converts the light into an electrical output signal, which is applied to logarithmic amplifier 704 and therefrom to integrator 706.

The integrators associated with the respective detectors are sampled at instants determined by the output pulses of encoder 130 to provide a plurality of transmission/absorption measurements, such measurements being converted to digital form and loaded into predetermined locations in a digital memory for further signal processing. As will be hereinafter more fully described, the respective motions of the sources and detectors in opposite directions along eccentric arcs provide absorption measurements over plural intersecting sets of parallel paths, from which measurements an absorption array can be generated utilizing the "parallel beam" algorithms noted above.

Mechanical rotation of gear 106, and hence sources 108, through only 120° provides a full 360° scan of the body section as will now be described in more detail. As noted above, the scanning operation develops a plurality of sets of a predetermined number of parallel absorption measurements, each successive parallel measurement being displaced with respect to the axes of the body section by a predetermined increment. The translation of the detectors along the arcs 114 effectively offsets angular motion between the detector and the irradiating source as the source rotates about the body section, each sample from a given detector thus being indicative of the absorption along a parallel path from the irradiating source. Each successive sample is, however, displaced with respect to the axes of the body section by an amount in accordance with the movement of the detectors (and sources).

In the presently preferred embodiment, with reference to FIGS. 8A–8G, conveyor 112 includes 192 detectors D0-D191, disposed at increments of 1° along the respective arcs of a predetermined radius with respect to the associated source (defined by the respective sections of track 114). Recalling that the arcs defined by track 114 substantially subtend the fan-angle (60°) of the X-ray beam, 60 detectors are illuminated at a given instant by each fan beam. Four detectors are inactive and disposed behind each source at any given instant. Accordingly, 180 detectors provide viable measurements at any given sampling instant.

Assuming that samples are taken every 1/6 of a degree of rotation by sources 108, in accordance with the output pulses of encoder 130 (FIG. 1) as a given detector traverses the 60° subtended by the arc defined by a section of track 114, the output signal thereof is integrated over 360 sampling periods and, since the fan beam irradiates the entire body section, the 360 parallel absorption measurements through the body section within a set are spaced apart at increments determined by the angular sampling interval (1/6°). It should be appreciated that the increments of distance between samples at the ends of the arc are slightly smaller than the increments at the center of the arc owing to the circular paths of sources 108. Conventional interpolation techniques, however, provide for computation of absorption along parallel paths at equally spaced increments for use in the aforementioned "parallel algorithms". For example, in the presently preferred embodiment, 320 uniformly spaced paths result from interpolation from some 360 actually measured paths. The presently preferred embodiment provides 360 of such sets of paths, each set being angularly oriented with respect to other sets in increments of 1°. The respective sets of paths will hereinafter be identified by the relative orientation angle of each set and a subscripted index indicative of the individual 360 possible path locations within each set.

In the simplest case, where a single detector is translated through the entire fan beam of one of the sources, the single detector provides an entire set of 360 parallel absorption measurements through the body section all at the same angle at which it was initially irradiated by the source However, where no single detector aligned at a given angle traverses an entire fan beam, two detectors cooperate to provide the complete set of 360 parallel measurements.

Sources 108 are disposed such that the leading edge (with respect to the direction of detector translation) of the beam irradiating a given section of track 114 intersects the trailing edge of the beam irradiating the immediately preceding track section by an angle of approximately 60°. Accordingly, each time a given detector, previously irradiated by a given source along a track section at a given angular orientation, passes behind a source and emerges on the adjacent track section for irradiation by an operationally adjacent source, the irradiation path orientation angle of the detector with respect to the upward vertical body section axis is increased by, accounting for the four detectors preceding the given detector behind the source, 56°.

Figure 8A:
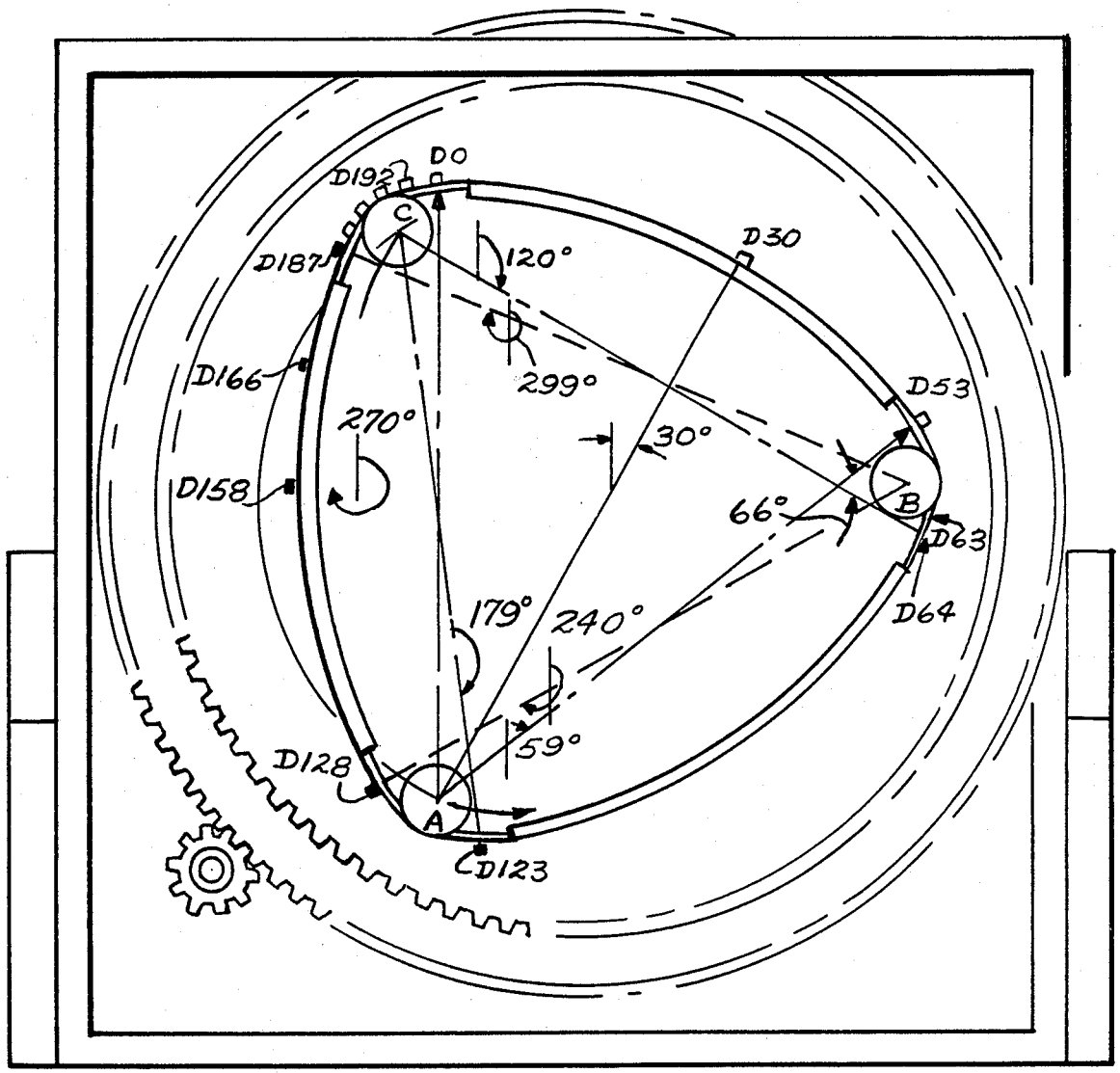
FIGS. 8A-8H are diagrams illustrating certain sequential positions in the operation of the scanner of FIG. 1.

For the purposes of the following discussion, it is assumed (1) that sources 108 rotate in a counterclockwise direction and conveyor 112 moves in a clockwise direction, (2) that the scan is initiated at an instant when a line drawn between the centers of sources 108A and 108C is substantially vertical, and (3) that detectors D0–D59, D64–D123 and D128–D187 are initially irradiated by sources 108A, 108C and 108B, respectively. Under these conditions the path orientations initially defined by detectors D0–D59, D64–D123 and D128–D187 are, respectively, 0°–59°, 120°–179°, and 240°–291° with respect to the upward vertical axis. Operation at a point about 1.5° after initiation of the scan is illustrated in FIG. 8A at this point, detector D0 is just beginning to be illuminated and, detectors 60–63, 124–127 and 188–191 are behind the respective sources 108.

As the scan proceeds, each individual detector provides measurements of absorption along successive parallel paths in a given set of such paths until such detector passes behind a source 108. For example, with specific reference to FIGS. 8A, 8B, 8C and 8D, as sources 108 rotate in a counterclockwise direction and conveyor 112 rotates in a clockwise direction, detector D0 traverses the arc between sources 108C and 108B, thus providing a full set of 360 parallel measurements at 0° ($0°_1$–$0°_{360}$) in cooperation with source 108A. Detectors D64 and D129 similarly traverse entire fan beams of sources 108C and 108B, respectively, to provide full sets of parallel measurements at 120° ($120°_1$–$120°_{360}$) and 240° ($240°_1$–$240°_{360}$). The remainder of the initially irradiated detectors provide only a partial set of parallel measurements at their respective initial angle before passing behind a source 108; detectors D1–D59, D65–D123 and D129–D187, respectively, in cooperation with sources 108A, 108C and 108B, provide partial sets of measurements at angles 1°–59°, 121°–179° and 241°–299°, respectively.

Figure 8B:
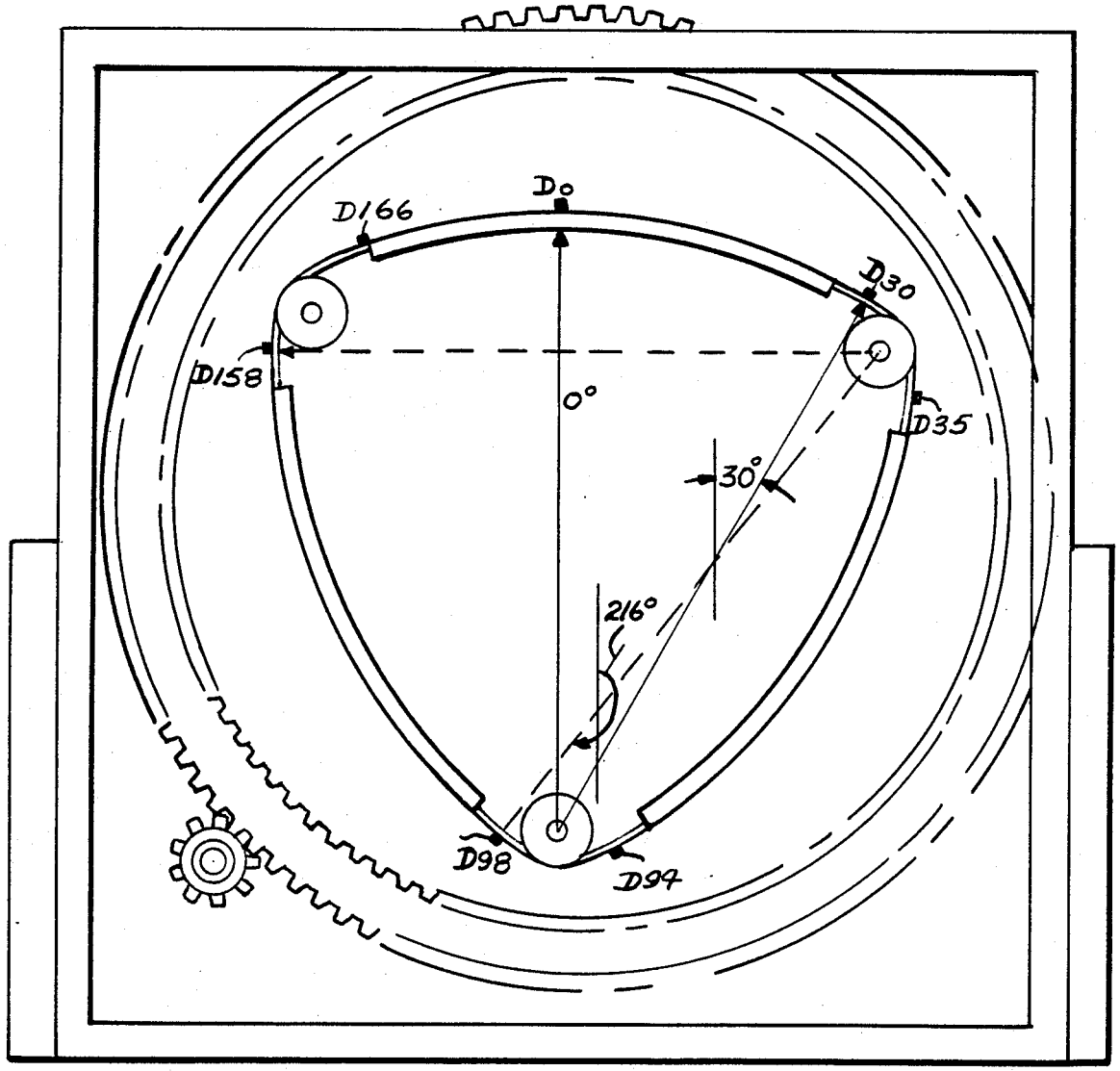
Figure 8C:
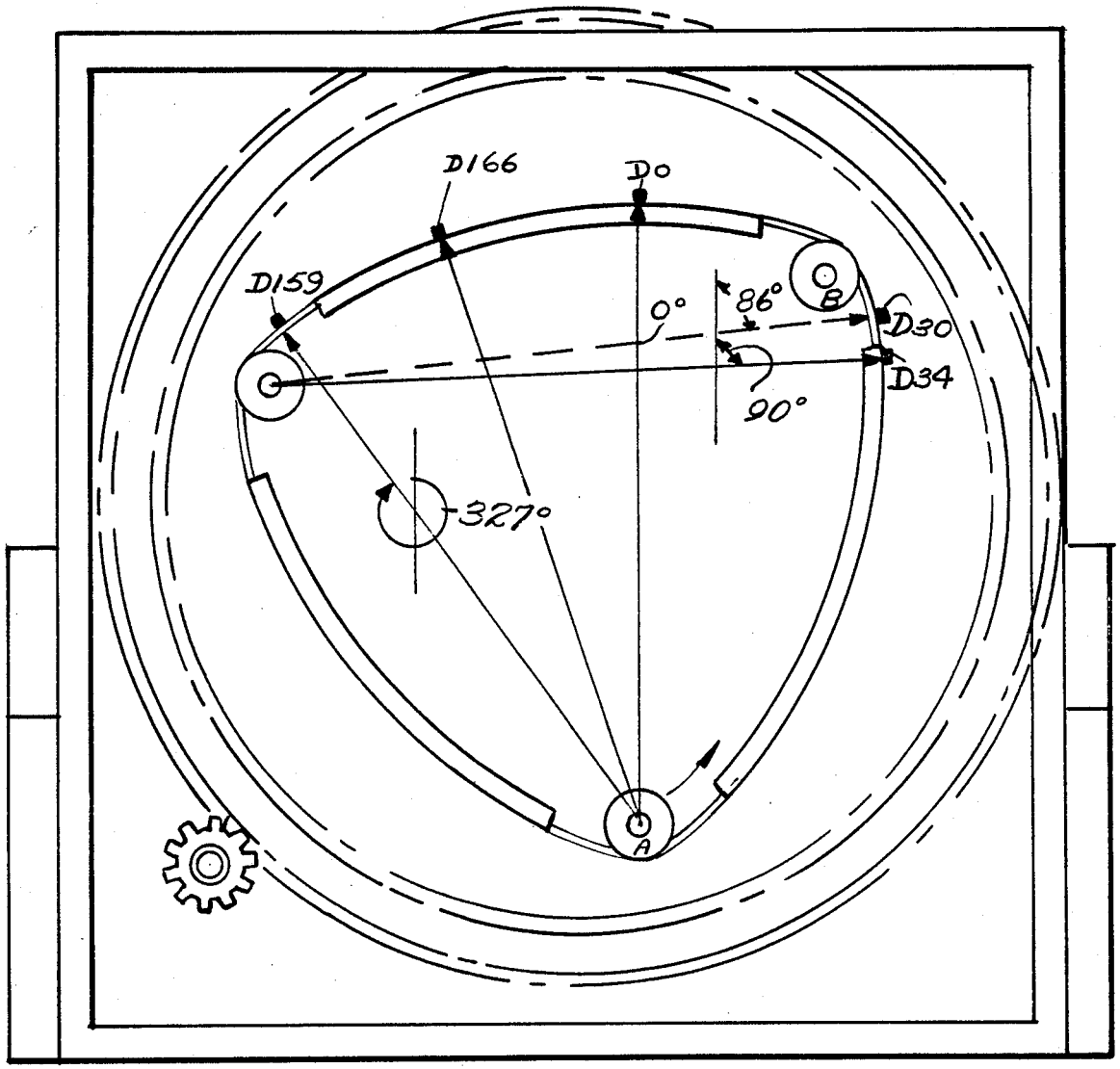
Figure 8D:
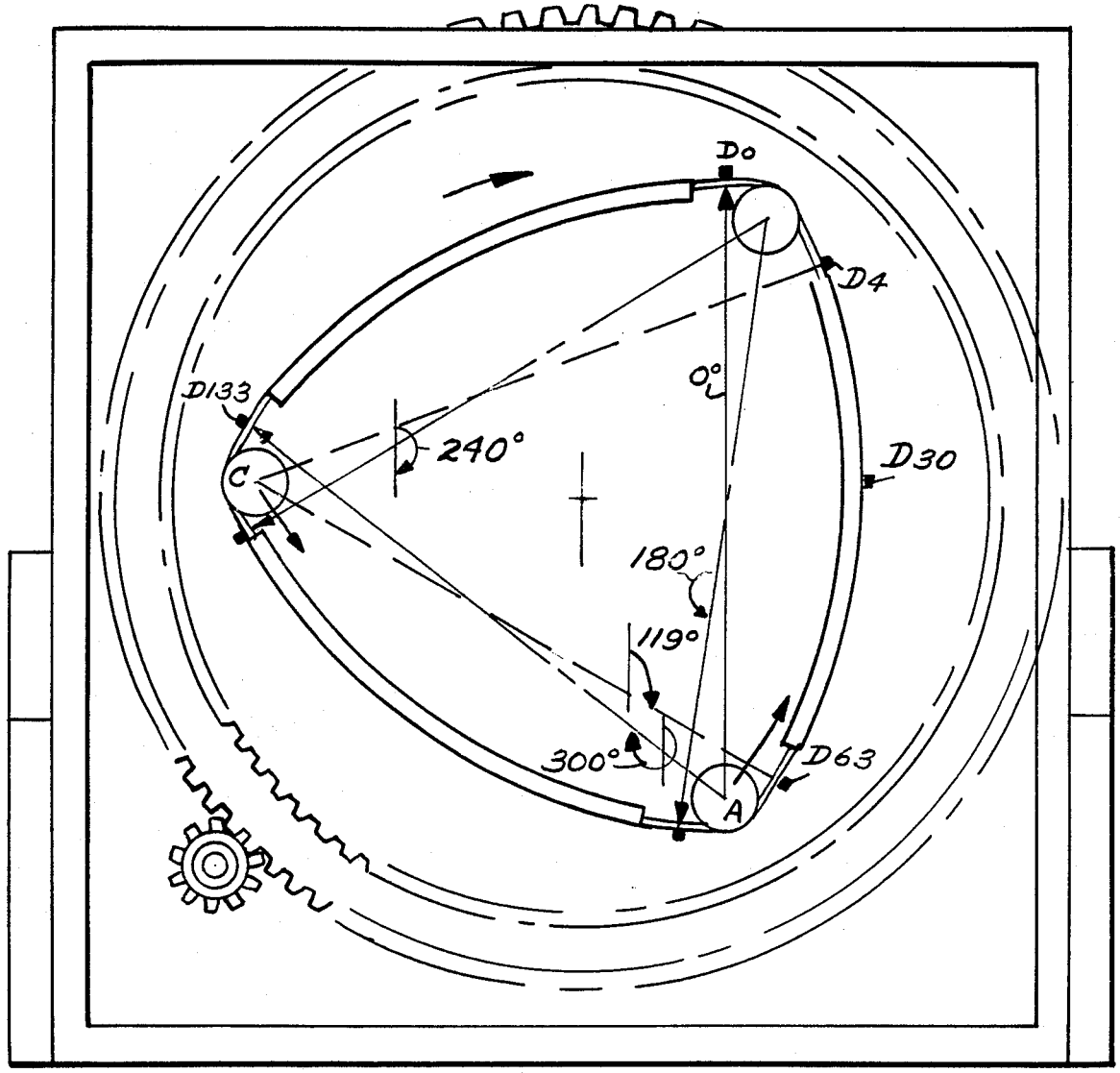
Figure 8E:
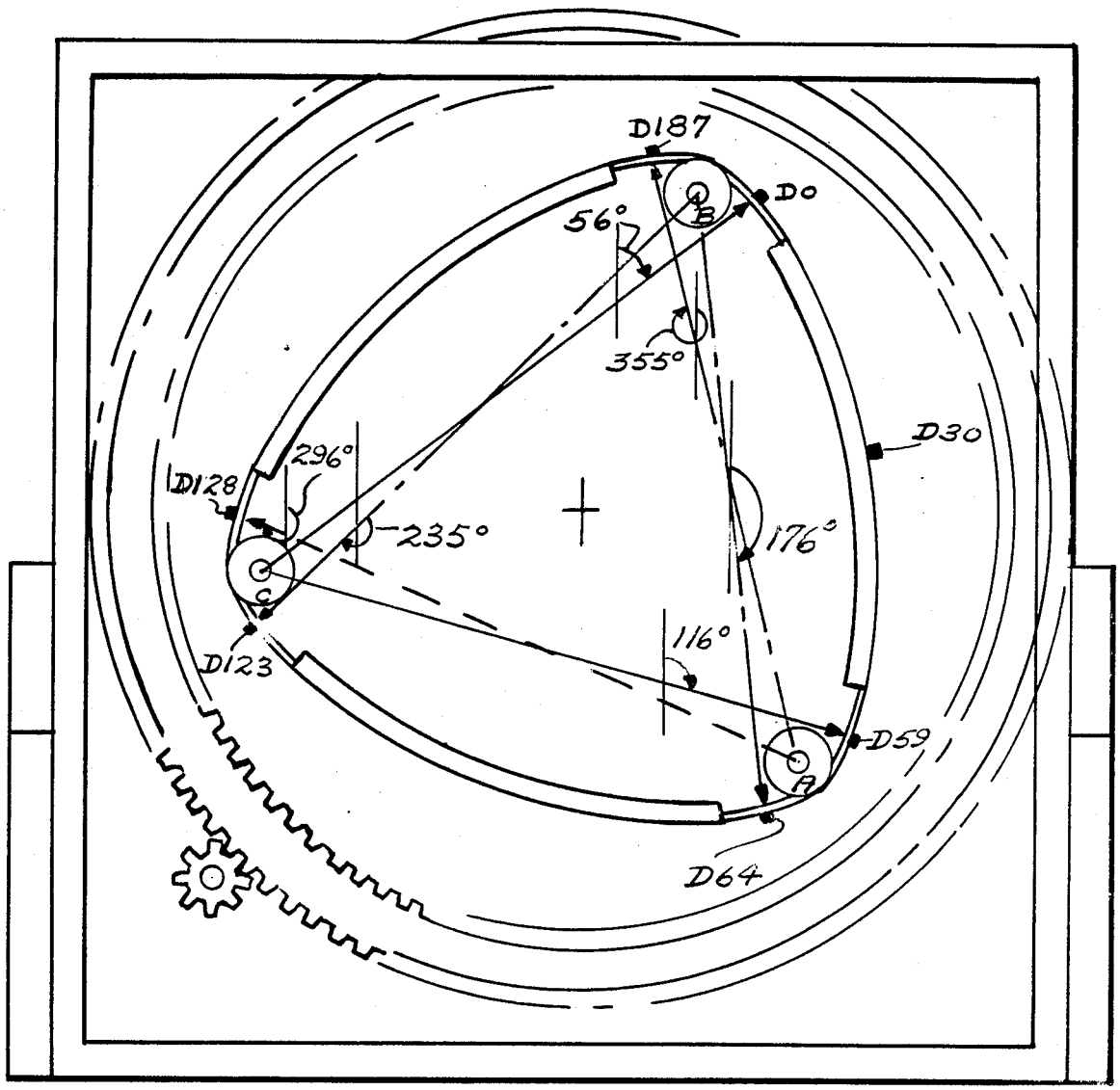
Figure 8F:
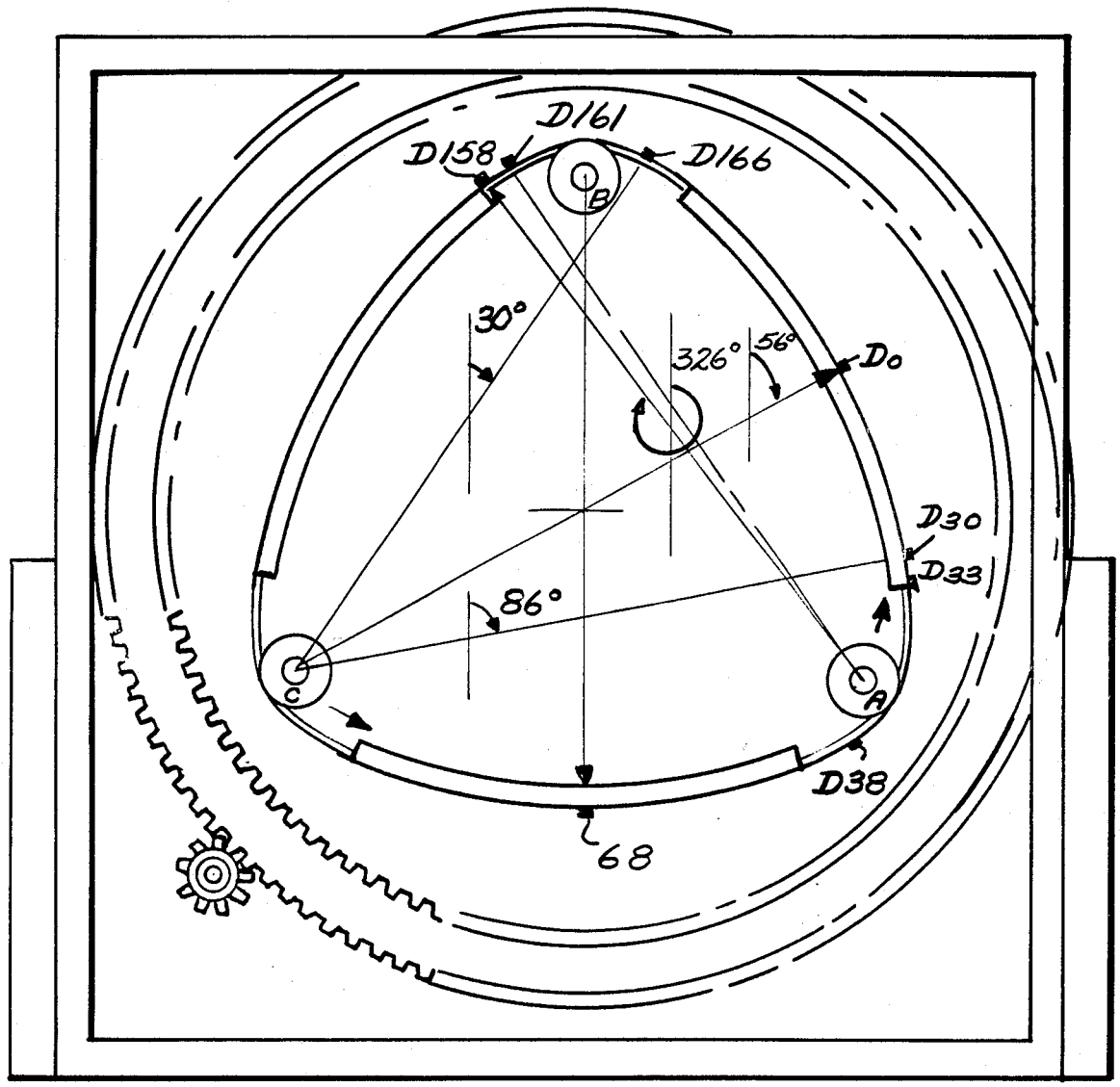
Figure 8G:
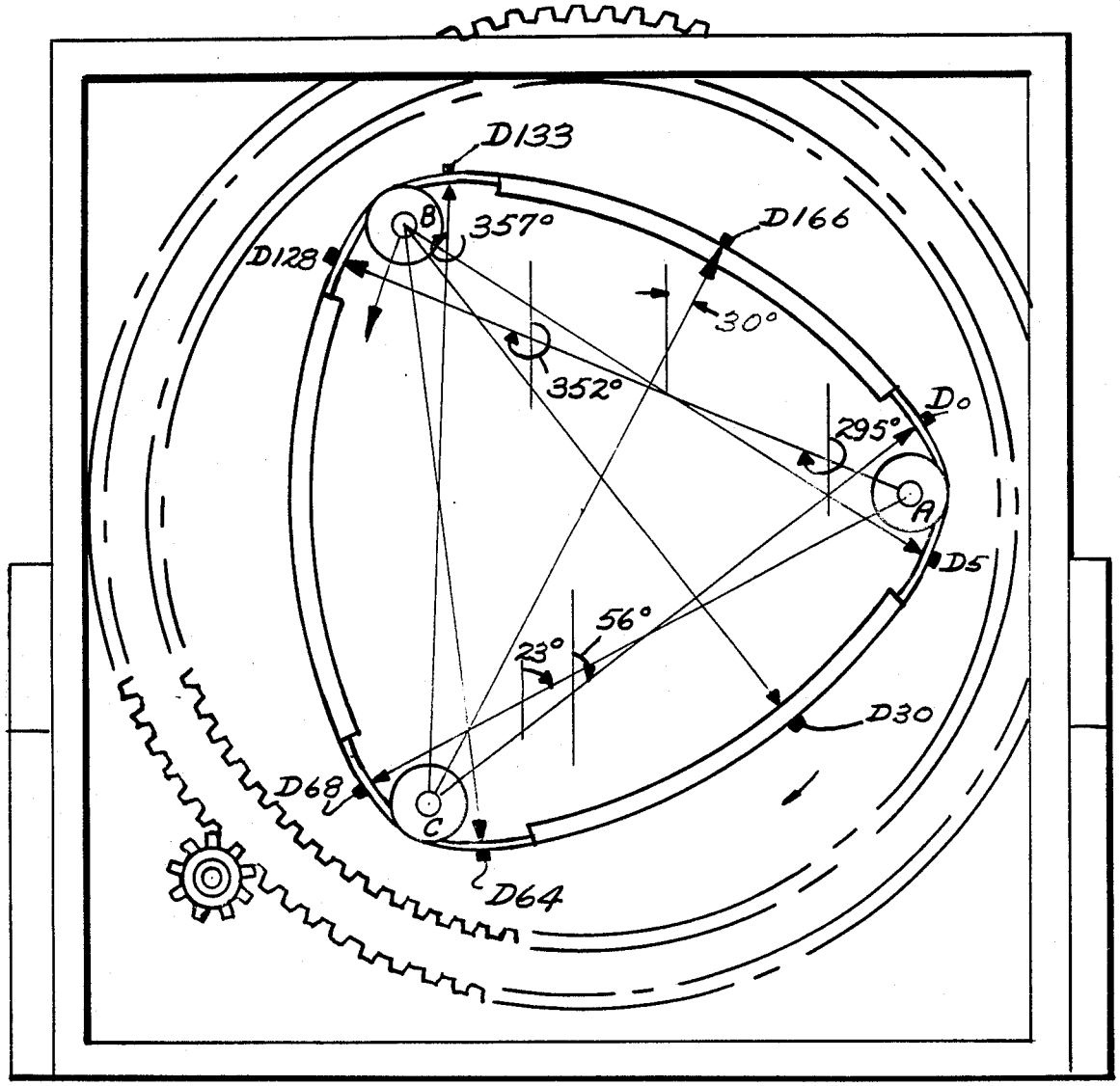
Figure 8H:
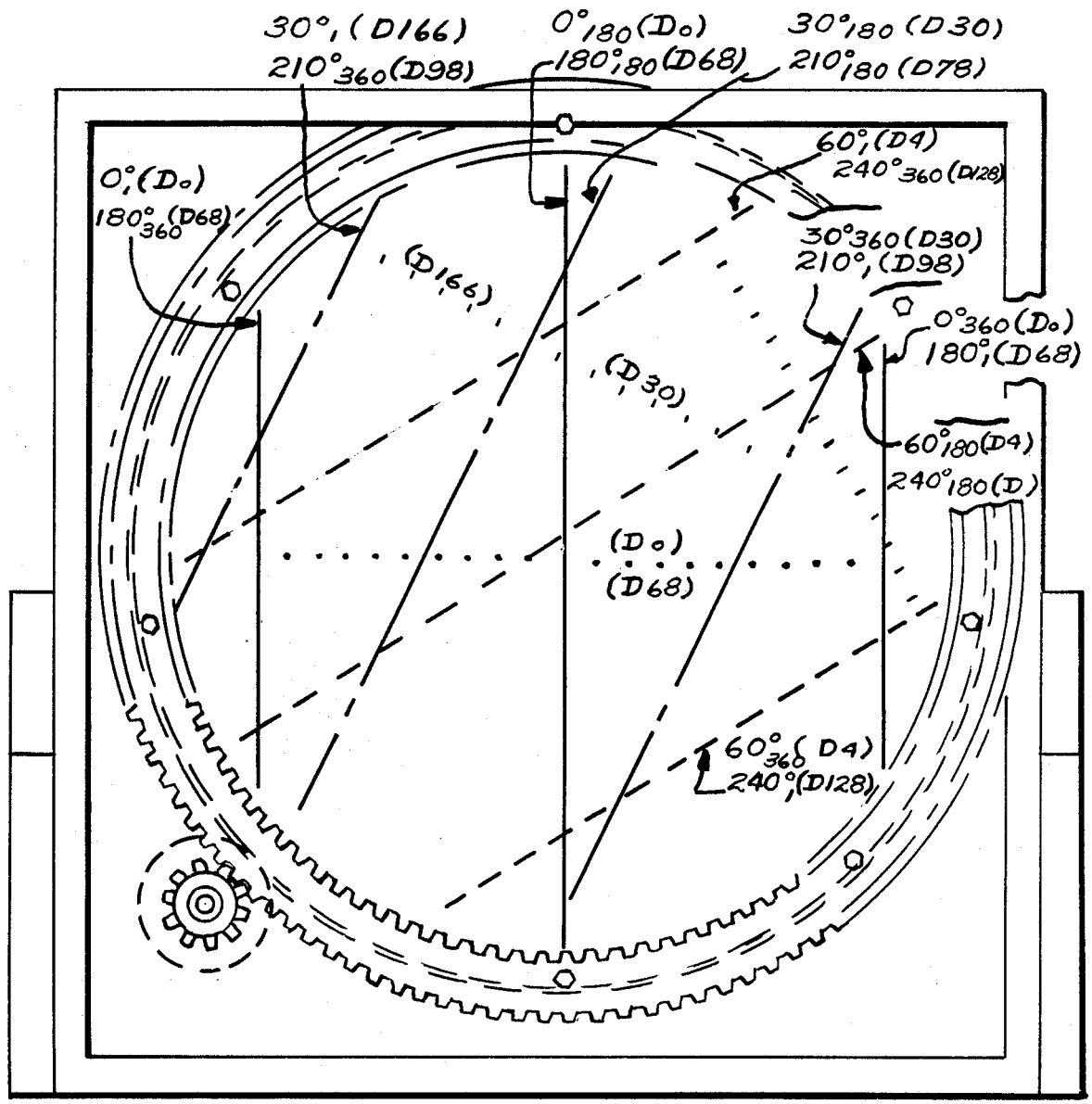

Upon emerging from behind the respective sources 108B, 108A and 108C, as illustrated in FIGS. 8E, 8F and 8G, detectors D0–D63, D64–D127 and D128–D191 traverse the fan beams of sources 108C, 108B and 108A, respectively, to provide complete sets of measurements along paths at 56°–119°, 176°–239 and 296°–359°. Detectors D5–D63, D69–D127 and D129–D191, in respective cooperation with sources 108B, 108A and 108C, further provide partial sets of measurements at 117°–175°, 237°–295° and 357°–55°, respectively. Thus, complete sets of 360 parallel measurements along paths oriented from 0° to 360° in one degree increments are provided by detectors as listed in Table I to provide 360 intersecting sets, each consisting of 360 parallel beam measurements, as illustrated (in part) in FIG. 8H.

TABLE I

| Parallel Path Set | provided by Detectors | from Source |
|---|---|---|
| 0° | D0 | 108A |
| 1°–55° | D137–D191/D1–D55 | 108C/108A |
| 56°–59° | D0–D3/D56–D59 | 108C/108A |
| 60°–119° | D4–D63 | 108C |
| 120° | D64 | 108C |
| 121°–179° | D9–D67/D65–D123 | 108B/108C |
| 180°–239° | D68–D127 | 108B |
| 240° | D128 | 108B |
| 241°–299° | D73–D131/D129–D187 | 108A/108B |
| 300°–359° | D132–D191 | 108A |

For example, the $30°_{180-360}$ paths of the set of paths oriented at 30° are provided by detector D30, in cooperation with source 108A (FIGS. 8A, 8B). The remainder of the set of paths oriented at 30° ($30°_{1-179}$) are provided by detector D166, in cooperation with source 108C.

It should be appreciated that paths at 180°–359° are equivalent to paths at 0°–179° with translational indices reversed; that is, $0°_{16}180°_{360}$ and $0°_{360}=180°_1$. Thus, dual measurements are taken along each path and are averaged to reduce artifacts and increase the accuracy of the eventual display.

In operation, sources 108 are initially brought to a stand-by condition (approximately one milliampere applied), an initial location is assigned in memory for the first 192 samples, and the scanner 100 is brought to a specific mechanical ready position, suitably detected by a limit switch affixed to rotating gear 106. The X-ray filaments of sources 108 are then energized and the motor 202 is activated. When rotating gear 106 reaches a predetermined "scan zero position" (sources 108A and 108C aligned vertically as in the previously described example), again suitably detected by a limit switch on gear 106, the operation of sources 108 is checked by measuring the filament current (90 ma) or sampling respective PMTs. Assuming the sources operational, the scan is initiated upon the leading edge of the next pulse from encoder 130. The respective PMT output signals are monitored continuously by logarithmic amplifiers 704 and integrators 706.

Integrator output signals are digitized and sampled every 1/6 degree rotated through by sources 108, each detector thus being sampled 384 times during the course of the ensuing 120° mechanical scan. Of these samples, only 360 are viable absorption measurements, the remaining 24 having been taken while the detector was located behind one of the sources 108. Such 24 samples are simply disregarded during processing. Integrators 706 are reset to zero after the respective channel of each is sampled. As noted above, two channel dual-slope integrators can be used to increase the sampling rate. The samples are digitized and loaded into predetermined locations in memory. After the scan is completed, interpolation can be performed to provide sets of measurements with equal increments between parallel paths. The data are then operated upon in accordance with a suitable conventional "parallel beam" algorithm, such as the convolution algorithm described in the aforementioned article by GN. Ramachandran et al, to develop an array of point-by-point relative absorption coefficients for the scanned body section. The array of absorption coefficients is then utilized to develop a visual display of the point-by-point relative absorption of the body section, as will be appreciated.

The scan is terminated upon 120° mechanical rotation of sources 108 from the scan zero position, suitably detected by a limit switch on gear 106, or a counter incremented by encoder pulses to a predetermined number. Failsafe mechanisms can also be provided.

The resultant complex motion of the individual detectors with respect to the sources is illustrated in FIG. 8I. Here the partial tracks of source 108A and detector DO are shown as parallel circular arcs. Source 108A clearly follows a circular arc 800 in going from its initial position (shown in solid lines) to position 108A' (shown in dotted lines) as should be apparent. In doing so, the angular direction of its fan-shaped beam will change as shown in FIG. 8I.

Since the detector DO is constrained to follow a path disposed at a constant distance from source 108A and is also constrained to point directly at source 108A while rotating thereabout, it follows that detector DO follows track B02 as seen in FIG. 8I. As indicated by an arrow, detector DO is constantly directed toward source 108A so as to provide measurements along parallel vertical paths during its travel while scanning through the fan-shaped beam from source 108A. This arrangement also permits the use of detector collimators and more sensitive scintillation crystals, etc. as previously pointed out. Similar operation is involved with the other detectors and sources (albeit at different angular orientations).

As illustrated in FIG. 8I, when only a single detector and source are considered, the resultant motion is analogous to the synchronous translation of a pencil beam source and detector pair as in earlier tomographic scanners so as to define plural parallel paths of given orientation. However, with this invention complete scanning is achieved much more quickly using a fan-shaped radiation beam and arrays of sources and detectors undergoing continuous motion. At the same time all the other described advantages are achieved to result in a clearly improved scanning method and apparatus.

It should be noted that while the various conductors shown interconnecting the elements in FIG. 7 are shown as single lines, they are not so shown in a limiting sense and may comprise plural connections as understood in the art.

In addition, it will be understood that the above description is of a presently preferred exemplary and illustrative embodiment of the present invention and that the invention is not limited to the specific form shown. Modifications may be made in the design and arrangement of the elements without departing from the spirit of the invention defined by the appended claims as will be apparent to those skilled in the art.

What is claimed is:

1. A tomographic scanner for scanning an area of interest, said tomographic scanner comprising:
    (a) a source of penetrating radiation;
    (b) first means for moving said source of penetrating radiation in a first arc which is subtended by an angle of at least approximately 120° centered on said source in the area of interest,
    (c) a detector array comprising an endless chain of detectors; and
    (d) second means for moving said detector array in a second arc which is subtended by an angle of at least approximately 120° centered on said source;
    (e) said first and second arcs being sized and shaped and said first and second means being adapted to cause said source and said detector array to move at velocities such that a plurality of parallel beam paths may be propagated from said source through said area to said detector array in each of a plurality of angular positions of said source and said detector array.

2. A tomographic scanner for scanning an area of interest comprising a penetrating radiation source moving in an arc encompassing said area of interest and a detector array comprising an endless chain of detectors moving in an arc encompassing said area of interest and circumscribing said source, said detector array moving in a direction opposite to the direction of said source so that a plurality of parallel beam paths are propagated from said source to said detector array over a plurality of angular positions through said area.

3. A tomographic scanner providing radiation beam absorption measurements taken along plural intersecting sets of substantially parallel paths within a cross-section of a three-dimensional body, said tomographic scanner comprising:
    a plurality of radiation sources disposed to direct respective fan-shaped beams of radiation through a desired cross-section of a three-dimensional body,
    said radiation sources being mounted for rotation in a first direction at least part-way around said three-dimensional body, and
    an array of radiation detectors disposed opposite said radiation sources for intercepting said fan-shaped beam of radiation after it has been partially absorbed by said
    said array of radiation detectors being mounted for rotation in a second direction opposite said first direction at least part-way around said three-dimensional body such that substantially parallel paths are defined between given individual detectors of the array and a given radiation source during the course of their oppositely directed movements,
    said plurality of radiation sources being spaced apart round the three-dimensional body and said array of radiation detectors substantially circumscribing said three-dimensional body such that a different segment of the array is disposed opposite each radiation source during each phase of said rotations;
    wherein said array of radiation detectors comprises an endless chain of individual detectors mounted for movement in a path circumscribing said plurality of radiation sources.

4. A tomographic scanner as in claim 3 wherein there are n radiation sources and wherein the movement required for complete scanning of the three-dimensional body is approximately 360/n degrees of rotational movement about an axis normal to said cross-section.

5. A method of tomographic scanning comprising:
    operating radiation sources to generate three fan-shaped beams of radiation each directed inwardly toward a desired cross-section of a three-dimensional body form spaced locations thereabout,
    rotating said three fan-shaped beams in a first direction and in unison at least part-way around said three-dimensional body,
    scanning different portions of the fan-shaped beams after passage through said three-dimensional body with a plurality of spaced-apart radiation detectors rotating in unison at least part-way around said three-dimensional body in a second direction generally opposite said first direction such that plural intersection sets of parallel paths are spaced locations, and measuring the radiation absorption experienced along said plural intersecting sets of parallel paths so as to provide data for use in constructing a visual depiction of said desired cross-section;

wherein said scanning step is performed along arcs disposed at substantially equal and constant distances from said radiation sources over respectively corresponding portions of the path of detector movement.

6. A method as in claim 5 wherein said rotating step is performed about an axis disposed within said three-dimensional body and substantially perpendicular to said fan-shaped beams.

7. A tomographic scanner providing radiation beam absorption measurements taken along plural intersecting sets of substantially parallel paths within a cross-section of three-dimensional body, said tomographic scanner comprising:

a plurality of radiation sources disposed to direct respective fan-shaped beams of radiation through a desired cross-section of a three-dimensional body, said radiation sources being mounted for rotation in a first direction at least part-way around said three-dimensional body, and an array of radiation detectors disposed opposite said radiation sources for intercepting said fan-shaped beam of radiation after it has been partially absorbed by said three-dimensional body, said array of radiation detectors being mounted for rotation in a second direction opposite said first direction at least part-way around said three-dimensional body such that substantially parallel paths are defined between give individual detectors of the array and a given radiation source during the course of their oppositely directed movement, said plurality of radiation sources being spaced apart around the three-dimensional body and said array of radiation detectors substantially circumscribing said three-dimensional body such that a different segment of the array is disposed opposite each radiation source during each phase of said rotations;

wherein said array of radiation detectors is mounted or movement along a corresponding plurality of circular arcs, each arc being centered on its respectively associated radiation source.

8. A tomographic scanner as in claim 7 wherein there are n radiation sources and wherein the movement required for complete scanning of the three-dimensional body is approximately 360/n degrees of rotational movement about an axis normal to said cross-section.

9. A tomographic a scanner as in claim 8 wherein there are n radiation sources and wherein the movement required for complete scanning of the three-dimensional body is approximately 360/n degrees of rotational movement about an axis normal to said cross-section.

10. A tomographic scanner providing radiation beam absorption measurements taken along plural intersecting sets of substantially parallel paths within a cross-section of a three-dimensional body, said tomographic scanner comprising:

a plurality of radiation sources disposed to direct respective fan-shaped beams of radiation through a desired cross-section of a three-dimensional body, said radiation sources being mounted for rotation in a first direction at least part-way around said three-dimensional body, and said array of radiation detectors disposed opposite said radiation sources for intercepting said fan-shaped beam of radiation after it has been partially absorbed by said three-dimensional body, said array of radiation detectors being mounted for rotation in a second direction opposite said first direction at least part-way around said three-dimensional body such that substantially parallel paths are defined between given individual detectors of the array and a given radiation source during the course of their oppositely directed movements, said plurality of radiation sources being spaced apart around the three-dimensional body and said array of radiation detectors substantially circumscribing said three-dimensional body such that a different segment of the array is disposed opposite each radiation source during each phase of said rotations;

wherein said array of radiation detectors is mounted for movement of each individual detector at a substantially constant distance from the radiation source then illuminating such individual detector during the course of their oppositely directed movements.

11. A tomographic scanner providing radiation beam absorption measurements taken along plural intersecting sets of substantially parallel paths within a cross-section of a three-dimensional body, said tomographic scanner comprising:

a radiation source disposed to direct a fan-shaped beam of radiation through a desired cross-section of a three-dimensional body, said radiation source being mounted for continuous rotation in a first direction around a substantial portion of said three-dimensional body, and an array of radiation detectors disposed opposite said radiation source for intercepting said fan-shaped beam of radiation after it has been partially absorbed by said three-dimensional body, said array of radiation detectors being mounted for continuous rotation in a second direction opposite said first direction around a substantial portion of said three-dimensional body, each individual detector being moved relative to said source across different portions of said fan-shaped beam such that substantially parallel paths are defined between give individual detectors of the array and the radiation source during the course of their oppositely directed movements;

wherein said array of radiation detectors is mounted for movement at a substantially constant distance from said radiation source over at least a portion of the path of movement.

12. A tomographic scanner comprising:

an aperture for accepting a three-dimensional body thereinto;

three radiation sources equally spaced apart about the circumference of a circle centered on said aperture, each radiation source being disposed to direct a fan-shaped substantially planar beam of radiation through a cross-section of said three-dimensional body and between the remaining two of said radiation sources;

said three radiation sources being fixedly mounted with respect to each other and mounted for rotation in unison in a first direction about an axis substantially perpendicular to the plane of said fan-shaped radiation beams;

an endless array of radiation detectors disposed on three intersecting paths, each path being situated between a pair of said radiation sources such that the detectors disposed on a path between two radiation sources intercept the fan-shaped radiation beam from the remaining third radiation source;

said endless array of radiation detectors being mounted for movement along said paths in a second direction opposite said first direction; and driving members coupled to said radiation sources and to said array of radiation detectors for driving them through their oppositely directed movements so as to define plural intersecting sets of substantially parallel paths between said radiation sources and the individual radiation detectors in said array.

13. A tomographic scanner as in claim 12 wherein said driving members are disposed for rotating said radiation sources through substantially 120 degrees at a substantially constant speed.

14. A tomographic scanner as in claim 13 wherein said driving members are disposed for moving said endless array of radiation detectors simultaneously and synchronously with said movement of the radiation sources.

15. A tomographic scanner s in claim 12 wherein each of said intersecting paths comprises an arc disposed at a substantially constant distance from its oppositely situated and respectively associated radiation source.

16. A tomographic scanner as in claim 12 comprising on the order of two hundred individual radiation detectors in said endless array of radiation detectors.

17. A tomographic scanner as in claim 12 wherein said endless array of radiation detectors comprises individual detectors mounted on sections of a flexibly-jointed endless chain circumscribing said three radiation sources.

18. A tomographic scanner as in claim 17 comprising rotatable guide members disposed about each radiation source guiding the endless chain from one intersecting path to be next and wherein said driving members include meshing toothed members disposed to automatically cause synchronous movement of the endless chain in response to rotational movement of the radiation sources.

19. A tomographic scanner as in claim 12 wherein said driving members are disposed for moving said endless array of radiation detectors simultaneously and synchronously with said movement of the radiation sources.

20. A tomographic scanner as in claim 19 Comprising on the order of two hundred individual radiation detectors in said endless array of radiation detectors.

21. A tomographic scanner as in claim 20 wherein said endless array of radiation detectors comprises individual detectors mounted on sections of a flexibly-jointed endless chain circumscribing said three radiation sources.

22. A tomographic scanner as in claim 12 further comprising:

signal processing means connected to each individual detector of said array of radiation detectors for constructing a visual depiction of said cross-section based upon radiation absorption measurements taken along plural intersecting sets of substantially parallel paths through said cross-section.

23. A method of tomographic scanning comprising:

rotating at least one substantially planar beam of radiation continuously in a first direction with respect to a three-dimensional body, and scanning the planar beam of radiation after passage through said three-dimensional body with a plurality of radiation detectors rotating continuously in a second direction generally opposite said first direction, each individual detector being moved relative to said beam across different portions of said planar beam so as to define plural intersecting sets of parallel paths, each set respectively corresponding to one of said detectors, along which parallel paths radiation absorption measurements may be taken;

wherein said scanning step comprises continuous movement along a portion of an arc situated at a constant distance from a source of said at least one substantially planar radiation beam.

24. A method as in claim 23 wherein said rotating step comprises continuous rotation through approximately 120 degrees of three equally spaced-apart radiation sources emanating co-planar fan-shaped beams, said rotation being about an axis which is substantially perpendicular to the plane of said fan-shaped beams.

25. A tomographic scanner providing radiation beam absorption measurements along plural substantially parallel paths within a cross-section of a three-dimensional body, said tomographic scanner comprising:

a plurality of radiation sources disposed to direct respective fan-shaped beams of radiation through a cross-section of a three-dimensional body;

said radiation sources being mounted for rotation in a first direction at least part-way around said three-dimensional body; and a plurality of radiation detectors disposed opposite said radiation sources for intercepting said fan-shaped beams of radiation after being partially absorbed by said three-dimensional body;

said radiation detectors being mounted for rotation in a second direction opposite said first direction at least part-way around said three-dimensional body such that the detectors successively scan different portions of the fan-shaped beams and define substantially parallel paths along which respectively corresponding successive radiation absorption measurements are thereby provided during the course of the oppositely directed movements of the radiation sources and radiation detectors, said plurality of radiation sources being spaced apart and around an aperture disposed to receive the three-dimensional body and being mounted for movement in unison thereabout; and said plurality of radiation detectors being mounted for movement in unison so as to substantially simultaneously define plural intersecting sets of substantially parallel paths within said cross-section;

said tomographic scanner further comprising means confining the movement of said radiation detectors to arcs of substantially constant and equal distances from opposingly disposed radiation sources over respectively corresponding portions of the path of movement.

26. A tomographic scanner as in claim 25 wherein said radiation sources are mounted for common rotational movement about an axis substantially perpendicular to their fan-shaped beams.

27. A tomographic scanner as in claim 25 wherein said radiation sources are mounted for common rotational movement about an axis substantially perpendicular to their fan-shaped beams.

28. A tomographic scanner as in claim 25 wherein each of said radiation detectors comprises a collimator for confining and more precisely defining said parallel paths thereby reducing the necessary radiation exposure experienced by the three-dimensional body.

29. A tomographic scanner as in claim 25 wherein said plurality of radiation detectors comprise an endless movable chain of individual inwardly directed detectors circumscribing said plurality of radiation sources.

30. A tomographic scanner as in claim 29 wherein said radiation sources are mounted for common rotational movement about an axis substantially perpendicular to their fan-shaped beams.

31. A tomographic scanner as in claim 29 wherein each of said radiation detectors comprises a collimator for confining and more precisely defining said parallel paths thereby reducing the necessary radiation exposure experienced by the three-dimensional body.

32. A tomographic scanner providing radiation beam absorption measurements along plural substantially parallel paths within a cross section of a three-dimensional body, said tomographic scanner comprising:
   at least one radiation source disposed to direct a fan-shaped beam of radiation through a cross-section of a three-dimensional body;
   said at least one radiation source being mounted for continuous rotation in a first direction around a substantial portion of said three-dimensional body; and
   at least one radiation detector disposed opposite said at least one radiation source for intercepting said fan-shaped beam of radiation after it has been partially absorbed by said three-dimensional body;
   said at last one radiation detector being mounted for continuous rotation in a second direction opposite said first direction around a substantial portion of said three-dimensional body while moving relative to said at least one source across different portions of said fan-shaped beam such that said at least one radiation detector successively scans different portions of the fan-shaped beam and defines substantially parallel paths along which respectively corresponding successive radiation absorption measurements are thereby provided during the course of the oppositely directed movements of said at least one radiation source and said at least one radiation detector;
   said tomographic scanner further comprising means confining the movement of said at least one radiation detector to an arc of substantially constant distance from said at least one radiation source over at least a portion of the path of movement.

33. A tomographic scanner as in claim 28 wherein said at least one radiation source is mounted for rotational movement about an axis substantially perpendicular to said fan-shaped beam.

34. A tomographic scanner as in claim 32 wherein said at least one radiation source is mounted for rotational movement about an axis substantially perpendicular to said fan-shaped beam.

35. A tomographic scanner as in claim 28 wherein said at least one radiation detector comprises a collimator for confining and more precisely defining said parallel paths thereby reducing the necessary radiation exposure experienced by the three-dimensional body.

36. A tomographic scanner as in claim 32 wherein said at least one radiation detector comprises a collimator for confining and more precisely defining said parallel paths thereby reducing the necessary radiation exposure experienced by the three-dimensional body.

37. A tomographic scanner providing radiation beam absorption measurements along plural substantially parallel paths within a cross-section of a three-dimensional body, said tomographic scanner comprising:
   a plurality of radiation sources disposed to direct respective fan-shaped beam as of radiation through a cross-section of a three-dimensional body;
   said radiation sources being mounted for rotation in a first direction at least part-way around said three-dimensional body; and
   a plurality of radiation detectors disposed opposite said radiation sources for intercepting said fan-shaped beams of radiation after being partially absorbed by said three-dimensional body;
   said radiation detectors being mounted for rotation in a second direction opposite said first direction at least part-way around said three-dimensional body such that the detectors successively scan different portion of the fan-shaped beams and defined substantially parallel paths along which respectively corresponding successive radiation absorption measurements are thereby provided during the course of the oppositely directed movements of the radiation sources and radiation detectors,
   said plurality of radiation sources being spaced apart and around an aperture disposed to receive the three-dimensional body and being mounted for movement in unison thereabout; and
   said plurality of radiation detectors being mounted for movement in unison so as to substantially simultaneously define plural intersecting sets of substantially parallel paths within said cross-section;
   wherein said plurality of radiation detectors comprises an endless movable chain of individual inwardly directed detectors circumscribing said plurality of radiation sources.

38. A tomographic scanner as in claim 37 wherein said plurality of radiation detectors takes radiation absorption measurements along each set of parallel paths, said radiation absorption measurements including a radiation absorption measurement taken with the radiation directed in both directions along each path within the set.

39. A tomographic scanner as in claim 30 wherein each of said radiation detectors comprises a collimetor for confining and more precisely defining said parallel paths thereby reducing the necessary radiation exposure experienced by the three-dimensional body.

40. A tomographic scanner as in claim 37 wherein said plurality of radiation detectors defines said plural intersecting sets of parallel paths during less than a complete revolution of a given radiation source about said three-dimensional body.

41. A tomographic scanner as in claim 40 wherein said plurality of radiation detectors takes radiation absorption measurements along each set of parallel paths, said radiation absorption measurements including a radiation absorption measurement taken with the radiation directed in both directions along each path within the set.

42. A tomographic scanner as in claim 37 wherein said radiation sources are mounted for common rotational movement about an axis substantially perpendicular to their fan-shaped beans.

43. A method of tomographic scanning a cross-section of a three-dimensional body and measuring radiation beam absorption therewith along a set of parallel paths to provide measurements which may be utilized in constructing a cross-sectional depiction of structures within the three-dimensional body having differing radiation absorption properties, said method comprising the steps of:
  directing a fan-shaped beam of radiation from a radiation source through a desired cross-section of a three-dimensional body,
  continuously rotating said radiation source with respect to said three-dimensional body in a first direction,
  scanning different portions of said fan-shaped beam with a radiation detector while rotating the radiation detector with respect to said radiation source in a second direction opposite said first direction such that a set of parallel paths are defined between the radiation detector and the radiation source during their oppositely directed movements, and
  measuring the radiation absorption encountered along thusly defined parallel paths;
  wherein said scanning step is performed at a substantially constant distance from said radiation source.

44. A method as in claim 43 wherein said scanning and measuring steps are performed simultaneously a predetermined number of times so as to provide simultaneous radiation absorption measurements along plural intersecting sets of parallel paths.

45. A method as in claim 44 wherein said rotating step comprises rotational movement about an axis disposed within said three-dimensional body and substantially perpendicular to said fan-shaped beam.

46. A method as claim 45 wherein said directing, rotating, scanning and measuring steps are simultaneously performed a predetermined number of times at spaced-apart positions circumscribing said three-dimensional body so as to reduce the necessary time for completing radiation absorption measurements along plural intersecting sets of parallel paths.

47. A method as in claim 46 wherein each of said predetermined number of scanning and measuring steps are replicated simultaneously at spaced apart detector locations circumscribing said three-dimensional body so as to provide simultaneous radiation absorption measurements along plural intersecting sets of parallel paths defined between predetermined detector and source locations.

48. A method as in claim 45 wherein said rotating step comprises rotational movement about an axis disposed within said three-dimensional body and substantially perpendicular to said fan-shaped beam.

49. A method of tomographic scanning comprising:
  rotating at least one substantially planar beam of radiation form at least one radiation source continuously in a first direction with respect to a three-dimensional body, and
  scanning the planar beam of radiation after passage through said three-dimensional body with a plurality of radiation detectors rotating continuously in a second direction generally opposite said first direction, each individual detector being moved relative to said beam across different portions of said planar beam so as to define plural intersecting sets of parallel paths, each set respectively corresponding to one of said detectors, along which parallel paths radiation absorption measurements may be taken;
  wherein said scanning step comprises continuous movement along the outer portions of intersecting arcs subtending substantially 120 degrees situated at equal constant distances from said at least one radiation source.

50. A method as in claim 49 wherein said rotating step comprises continuous rotation through approximately 120 degrees of three equally spaced-apart radiation sources emanating co-planar fan-shaped beams, said rotation being about an axis which is substantially perpendicular to the plane of said fan-shaped beams.

51. Apparatus for providing a plurality of sets of parallel absorption measurements through a body section comprising:
  a radiation source for producing a fan-beam to irradiate said body section;
  a plurality of radiation detectors, disposed on an arc of predetermined constant radius form said source, for producing indices of the absorption of radiation by said body section along respective paths oriented at respective predetermined angles with respect to said body section;
  means for moving said source about said body section; and
  means for translating said detectors in a direction and at a rate to effectively offset any angular deviation of the path between the respective detector means and said source from said respective predetermined angles.

52. The apparatus of claim 51 further comprising:
  means for periodically sampling said detector indicia in accordance with timing signals applied thereto; and
  encoder means for generating a pulse in response to said rotating source rotating through a predetermined incremental angle, said encoder pulse being applied to said sampling means as said timing signals.

53. The apparatus of claim 51 wherein said detectors each comprise a scintillation crystal and a photomultiplier tube optically coupled thereto, power to and signals from said photomultiplier tube being communicated on electrical conductors, and wherein said apparatus further comprises:
  carriage means, adapted for rotation in substantial synchronization with said detectors, for maintaining the relative disposition of said detectors and said conductors.

54. The apparatus of claim 51 wherein aid detectors include collimators whereby said detectors are substantially non-responsive to radiation along paths different from said respective path oriented at said predetermined angle.

55. The apparatus of claim 54 including three of said radiation sources, relatively disposed at 120 about said body section adapted for rotation unison about said body section; said plurality of detectors being mutually connected in an endless chain, disposed about said body section outwardly of said sources.

56. The apparatus of claim 55 further including:
  three arcuate tracks, each subtending the fan-beam of an associated one of said sources at a predetermined radius from said associated source;

said tracks being disposed outwardly of said sources and adapted for rotation in unison with said sources;

said endless chain of detectors being disposed for translation along said tracks.

57. Apparatus for providing a plurality of sets of parallel absorption measurements through a body section comprising:

three radiation sources for producing respective fan-beams to irradiate said body section, said sources being relatively disposed at 120° intervals about said body section and adapted for rotation in unison about said body section, a plurality of radiation detectors mutually connected in an endless chain and disposed about said body section outwardly of said sources on plural arcs of predetermined radius from said sources, for producing indices of the absorption of radiation by said body section along respective paths oriented at respective predetermined angles with respect to said body section, means for moving said sources about said body section; and means for translating said detectors in a direction and at a rate to effectively offset any angular deviation of the path between the respective detector means and said source from said respective predetermined angles.

58. The apparatus of claim 57 further including:
three arcuate tracks, each subtending the fan-beam of an associated one of said sources at a predetermined radius form said associated source;

said track being disposed outwardly of said sources and adapted for rotation in unison with said sources;

said endless chain of detectors being disposed for translation along said tracks.

59. A tomographic scanner comprising:
at least one radiation source providing a fan-shaped beam of radiation, an array of radiation detectors directed to receive radiation from said source, said radiation source and individual ones of said radiation detectors being mounted for continuous motion along curvilinear loci separated by a constant distance as measured along spaced-apart parallel lines and said individual ones of said radiation detectors being moved across different portions of said fan-shaped beam and constantly directed along successive parallel radiation beam paths at said radiation source during such motion.

60. A tomographic scanner as in claim 59 wherein said radiation source rotates about an axis and said array of radiation detectors move along a circular arc centered on said radiation source.

61. A tomographic scanner as in claim 59 wherein said radiation source rotates about a first axis and said individual detectors rotate about a second axis passing through said radiation source.

62. A tomographic scanner as in claim 59 wherein said individual detectors comprise a calcium fluoride scintillation crystal.

63. A tomographic scanner as in claim 59 further comprising a radiation collimator mounted in association with each individual radiation detector and defining individual radiation passing paths between said radiation source and the respective individual detectors.

64. A tomographic scanner as in claim 63 wherein said individual detectors comprise a calcium fluoride scintillation crystal.

65. A tomographic scanner as in claim 59 wherein said parallel loci are circular arcs.

66. A tomographic scanner as in claim 65 further comprising a radiation collimator mounted in association with each individual radiation detector and defining individual radiation paths passing between said radiation source and the respective individual detectors.

67. A tomographic scanner as in claim 66 wherein said radiation source rotates about an axis and said array of radiation detectors move along a circular arc centered on said radiation source.

68. A tomographic scanner as in claim 67 wherein said individual detectors comprise a calcium fluoride scintillation crystal.

69. A tomographic scanner as in claim 66 wherein said radiation source rotates about a first axis and said individual detectors rotate about a second axis passing through said radiation source.

70. A tomographic scanner as in claim 69 wherein said individual detectors comprise a calcium fluoride scintillation crystal.

71. A method of tomographic scanning comprising:
directing at least one fan-shaped beam of radiation towards a three-dimensional body under examination, scanning said beam of radiation about said body along a first curvilinear locus, scanning at least one radiation detector through different portions of said beam along a second curvilinear locus constantly spaced from said first locus, as measured along spaced-apart parallel lines, while maintaining a constant orientation of the detector with respect to the source of said radiation beam so as to define plural parallel radiation paths between the source and the detector during said scanning motion.

72. A method of tomographic scanning as in claim 71 wherein said first and second loci are circular arcs disposed respectively on opposing sides of said body.

73. A method of tomographic scanning as in claim 71 further comprising the step of collimating the radiation directed toward the detector.

74. A method of tomographic scanning as in claim 71 wherein an array of individual radiation detectors are simultaneously scanned.

75. A method of tomographic scanning as in claim 74 further comprising the step of collimating the radiation directed toward each individual detector.

76. A method of tomographic scanning as in claim 74 wherein plural beams are simultaneously scanned and wherein successive respectively corresponding portions of the detector array are simultaneously scanned with respect to each beam source.

77. A method of tomographic scanning as in claim 76 further comprising the step of collimating the radiation directed toward each individual detector.

78. A method of tomographic scanning as in claim 71 wherein the source of said radiation beam is rotated about an axis passing through said body and wherein said radiation detector is rotated about an axis passing through said source.

79. A method of tomographic scanning as in claim 78 further comprising the step of collimating the radiation directed toward the detector.

80. A method of tomographic scanning as in claim 78 wherein an array of individual radiation detectors are simultaneously scanned.

81. A method of tomographic scanning as in claim 80 further comprising the step of collimating the radiation directed toward each individual detector.

82. A method of tomographic scanning as in claim 80 wherein plural beams are simultaneously scanning and wherein successive respectively corresponding portions of the detector array are simultaneously scanned with respect to each beam source.

83. A method of tomographic scanning as in claim 82 further comprising the step of collimating the radiation directed toward each individual detector.

84. A tomographic scanner providing radiation beam absorption measurements taken along plural intersecting sets of substantially parallel paths within a cross-section of a three-dimensional body, said tomographic scanner comprising:

a radiation source disposed to direct a a fan-shaped beam of radiation through a desired cross-section of a three-dimensional body, said radiation source being mounted for continuous rotation in a first direction around a substantial portion of said three-dimensional body, and an array of radiation detectors disposed opposite said radiation source for intercepting said fan-shaped beam of radiation after it has been partially absorbed by said three-dimensional body, said array of radiation detectors being mounted for continuous rotation in a second direction opposite said first direction around a substantial portion of said three-dimensional body, each individual detector being moved relative to said source across different portions of said fan-shaped beam such that substantially parallel paths are defined between given individual detectors of the array and the radiation source during the course of their oppositely directed movements;

wherein said array of radiation detectors is mounted for movement along a circular arc centered on said radiation source.

* * * * *